United States Patent
Richardson et al.

(10) Patent No.: US 9,314,030 B2
(45) Date of Patent: Apr. 19, 2016

(54) PARTICULATE WOOD PRESERVATIVE AND METHOD FOR PRODUCING SAME

(71) Applicant: Koppers Performance Chemicals Inc., Pittsburgh, PA (US)

(72) Inventors: H. Wayne Richardson, Sumter, SC (US); Robert L. Hodge, Sumter, SC (US)

(73) Assignee: Koppers Performance Chemicals Inc., Pittsburgh, PA (US)

( * ) Notice: Subject to any disclaimer, the term of this patent is extended or adjusted under 35 U.S.C. 154(b) by 74 days.

(21) Appl. No.: 14/226,484

(22) Filed: Mar. 26, 2014

(65) Prior Publication Data

US 2015/0056258 A1  Feb. 26, 2015

Related U.S. Application Data

(63) Continuation of application No. 13/446,373, filed on Apr. 13, 2012, now Pat. No. 8,722,198, which is a continuation of application No. 12/209,653, filed on Sep. 12, 2008, now Pat. No. 8,158,208, which is a continuation of application No. 10/961,206, filed on Oct. 12, 2004, now abandoned.

(60) Provisional application No. 60/616,646, filed on Oct. 8, 2004, provisional application No. 60/571,535, filed on May 17, 2004.

(51) Int. Cl.
| | |
|---|---|
| A01N 25/00 | (2006.01) |
| A01N 59/00 | (2006.01) |
| A01N 59/20 | (2006.01) |
| A01N 25/02 | (2006.01) |
| A01N 59/16 | (2006.01) |
| A01N 25/04 | (2006.01) |
| A01N 25/08 | (2006.01) |
| A01N 25/12 | (2006.01) |
| C09D 5/14 | (2006.01) |
| A01N 33/00 | (2006.01) |
| A01N 33/26 | (2006.01) |
| A01N 43/00 | (2006.01) |
| A01N 29/10 | (2006.01) |
| A01N 31/08 | (2006.01) |
| A01N 31/14 | (2006.01) |
| A01N 57/00 | (2006.01) |
| A01N 57/06 | (2006.01) |
| A01N 57/10 | (2006.01) |
| A01N 57/14 | (2006.01) |
| A01N 57/16 | (2006.01) |

(52) U.S. Cl.
CPC .............. *A01N 59/20* (2013.01); *A01N 25/00* (2013.01); *A01N 25/02* (2013.01); *A01N 25/04* (2013.01); *A01N 25/08* (2013.01); *A01N 25/12* (2013.01); *A01N 33/00* (2013.01); *A01N 33/26* (2013.01); *A01N 59/00* (2013.01); *A01N 59/16* (2013.01); *C09D 5/14* (2013.01); *A01N 29/10* (2013.01); *A01N 31/08* (2013.01); *A01N 31/14* (2013.01); *A01N 43/00* (2013.01); *A01N 57/00* (2013.01); *A01N 57/06* (2013.01); *A01N 57/10* (2013.01); *A01N 57/14* (2013.01); *A01N 57/16* (2013.01)

(58) Field of Classification Search
None
See application file for complete search history.

(56) References Cited

U.S. PATENT DOCUMENTS

| | | | |
|---|---|---|---|
| 1,388,513 | A | 8/1921 | Chandler |
| 1,999,458 | A | 4/1935 | Hollister |
| 2,558,304 | A | 6/1951 | Marcot et al. |
| 3,007,844 | A | 11/1961 | Schulz |
| 3,087,936 | A | 4/1963 | Le Suer et al. |
| 3,231,464 | A | 1/1966 | Dettwiler et al. |
| 3,254,025 | A | 5/1966 | Le Suer et al. |
| 3,321,464 | A | 5/1967 | Oberley |
| 3,443,881 | A | 5/1969 | Hudson |
| 3,535,423 | A | 10/1970 | Ordas |
| 3,622,377 | A | 11/1971 | Conner |
| 3,816,307 | A | 6/1974 | Woods |

(Continued)

FOREIGN PATENT DOCUMENTS

| | | |
|---|---|---|
| AU | B-15117/92 | 10/1992 |
| AU | 646732 B2 | 3/1994 |

(Continued)

OTHER PUBLICATIONS

Panshin et al., "Textbook of Wood Technology: Structure, Identification, Properties, and Uses of Commercial Woods of the United States and Canada, 4th Edition," Copyright 1980 by McGraw-Hill, Inc., p. 113.*

(Continued)

*Primary Examiner* — William Phillip Fletcher, III
(74) *Attorney, Agent, or Firm* — Covington & Burling LLP

(57) ABSTRACT

A wood preservative includes injectable particles comprising one or more sparingly soluble copper salts. The copper-based particles are sufficiently insoluble so as to not be easily removed by leaching but are sufficiently soluble to exhibit toxicity to primary organisms primarily responsible for the decay of the wood. Exemplary particles contain for example copper hydroxide, basic copper carbonate, copper carbonate, basic copper sulfates including particularly tribasic copper sulfate, basic copper nitrates, copper oxychlorides, copper borates, basic copper borates, and mixtures thereof. The particles typically have a size distribution in which at least 50% of particles have a diameter smaller than 0.25 μm, 0.2 μm, or 0.15 μm. At least about 20% and even more than 75% of the weight of the particles may be composed of the substantially crystalline copper salt. Wood or a wood product may be impregnated with copper-based particles of the invention.

15 Claims, 3 Drawing Sheets

(56) References Cited

U.S. PATENT DOCUMENTS

Figures 1, 1A, 1B:
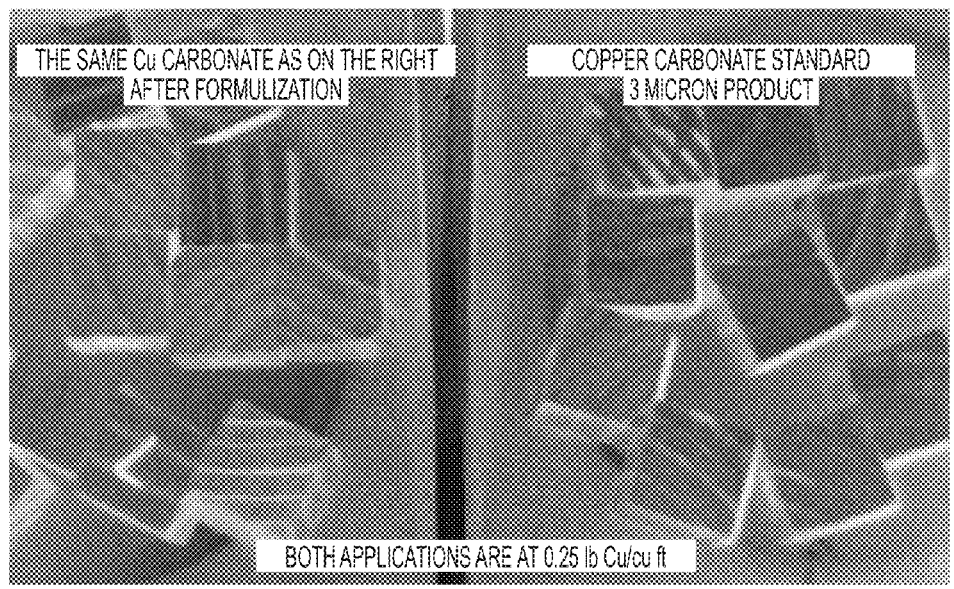

| | | | |
|---|---|---|---|
| 3,837,875 A | 9/1974 | Murphy | |
| 3,874,891 A | 4/1975 | Grobmann et al. | |
| 3,945,835 A | 3/1976 | Clarke et al. | |
| 3,957,494 A | 5/1976 | Oberley | |
| 3,968,276 A | 7/1976 | Allen | |
| 4,003,994 A | 1/1977 | Downer et al. | |
| 4,058,607 A | 11/1977 | Hennart et al. | |
| 4,061,770 A | 12/1977 | Marks | |
| 4,062,991 A | 12/1977 | Kyte et al. | |
| 4,075,325 A | 2/1978 | Kauzal | |
| 4,075,326 A | 2/1978 | Kuyama et al. | |
| 4,089,999 A | 5/1978 | Mondt et al. | |
| 4,142,009 A | 2/1979 | Kyte et al. | |
| 4,172,904 A | 10/1979 | Young et al. | |
| 4,220,688 A | 9/1980 | Mitchell et al. | |
| 4,310,590 A | 1/1982 | Petigara | |
| 4,313,976 A | 2/1982 | Leach | |
| 4,339,617 A | 7/1982 | Imai et al. | |
| 4,404,169 A | 9/1983 | Ploss et al. | |
| RE31,576 E | 5/1984 | Hilditch | |
| 4,456,486 A | 6/1984 | Bernhard | |
| 4,507,152 A | 3/1985 | Collins et al. | |
| 4,539,047 A | 9/1985 | Crockatt et al. | |
| 4,596,694 A | 6/1986 | Rozmus | |
| 4,597,730 A | 7/1986 | Rozmus | |
| 4,622,248 A | 11/1986 | Leach et al. | |
| RE32,329 E | 1/1987 | Paszner | |
| 4,649,065 A | 3/1987 | Hein et al. | |
| 4,650,792 A | 3/1987 | Underwood | |
| 4,663,364 A | 5/1987 | Iwasaki et al. | |
| 4,670,430 A | 6/1987 | Imamura et al. | |
| 4,698,099 A | 10/1987 | Nakamura et al. | |
| 4,702,776 A | 10/1987 | Hoffner et al. | |
| 4,720,514 A | 1/1988 | Needham | |
| 4,737,491 A | 4/1988 | Leppavuori et al. | |
| 4,741,971 A | 5/1988 | Beck et al. | |
| 4,752,297 A | 6/1988 | Leach | |
| 4,808,406 A | 2/1989 | Brinkman | |
| 4,857,214 A | 8/1989 | Papay et al. | |
| 4,857,365 A | 8/1989 | Hirao et al. | |
| 4,872,916 A | 10/1989 | Latosky | |
| 4,897,427 A | 1/1990 | Barnavon et al. | |
| 4,923,894 A | 5/1990 | Kanda et al. | |
| 4,950,221 A | 8/1990 | Gordon | |
| 4,961,865 A | 10/1990 | Pennartz | |
| 4,986,851 A | 1/1991 | Dietz et al. | |
| 4,988,545 A | 1/1991 | Laks | |
| 5,030,285 A | 7/1991 | Vallvey et al. | |
| 5,049,677 A | 9/1991 | Prout et al. | |
| 5,098,472 A | 3/1992 | Watkins et al. | |
| 5,110,822 A | 5/1992 | Sherba et al. | |
| 5,130,463 A | 7/1992 | Haubennestel et al. | |
| 5,145,684 A | 9/1992 | Liversidge et al. | |
| 5,147,686 A | 9/1992 | Ichimura et al. | |
| 5,151,218 A | 9/1992 | Haubennestel et al. | |
| 5,186,947 A | 2/1993 | Goettsche et al. | |
| 5,196,407 A | 3/1993 | Goletz et al. | |
| 5,198,133 A | 3/1993 | Papay | |
| 5,200,421 A | 4/1993 | Ludwig et al. | |
| 5,207,823 A | 5/1993 | Shiozawa | |
| 5,277,979 A | 1/1994 | Kielbania, Jr. et al. | |
| 5,304,376 A | 4/1994 | Friedrichs et al. | |
| 5,342,438 A | 8/1994 | West | |
| 5,360,783 A | 11/1994 | Itoh et al. | |
| 5,424,077 A | 6/1995 | Lajoie | |
| 5,438,034 A | 8/1995 | Walker | |
| 5,462,589 A | 10/1995 | Nicholas et al. | |
| 5,462,931 A | 10/1995 | Shaber et al. | |
| 5,470,585 A | 11/1995 | Gilchrist | |
| 5,478,598 A * | 12/1995 | Shiozawa | B27K 3/15 106/15.05 |
| 5,484,934 A | 1/1996 | Ikeda et al. | |
| 5,527,384 A | 6/1996 | Williams et al. | |
| 5,527,423 A | 6/1996 | Neville et al. | |
| 5,527,816 A | 6/1996 | Shaber et al. | |
| 5,536,305 A | 7/1996 | Yu | |
| 5,552,378 A | 9/1996 | Trinh et al. | |
| 5,582,638 A | 12/1996 | Coutelle et al. | |
| 5,624,916 A | 4/1997 | Shaber et al. | |
| 5,635,217 A | 6/1997 | Goettsche et al. | |
| 5,667,795 A | 9/1997 | Fraley et al. | |
| 5,693,644 A | 12/1997 | Teramae et al. | |
| 5,714,507 A | 2/1998 | Valcke et al. | |
| 5,763,364 A | 6/1998 | Frisch et al. | |
| 5,833,741 A | 11/1998 | Walker | |
| 5,855,662 A | 1/1999 | Brand et al. | |
| 5,874,025 A | 2/1999 | Heuer et al. | |
| 5,874,456 A | 2/1999 | McDade | |
| 5,874,476 A | 2/1999 | Hsu et al. | |
| 5,879,025 A | 3/1999 | Blumenthal | |
| 5,916,356 A | 6/1999 | Williams et al. | |
| 5,961,843 A | 10/1999 | Hayakawa et al. | |
| 5,972,266 A | 10/1999 | Fookes et al. | |
| 5,990,043 A | 11/1999 | Kugler et al. | |
| 6,033,648 A | 3/2000 | Candau | |
| 6,074,986 A | 6/2000 | Mulqueen et al. | |
| 6,110,263 A | 8/2000 | Goettsche et al. | |
| 6,123,756 A | 9/2000 | Poppen et al. | |
| 6,139,879 A | 10/2000 | Taylor | |
| 6,143,318 A | 11/2000 | Gilchrist et al. | |
| 6,250,350 B1 | 6/2001 | Muraki et al. | |
| 6,274,199 B1 | 8/2001 | Preston et al. | |
| 6,303,183 B1 | 10/2001 | Wilczynski et al. | |
| 6,306,201 B1 | 10/2001 | Makino | |
| 6,306,202 B1 | 10/2001 | West | |
| 6,306,939 B1 | 10/2001 | Gupta et al. | |
| 6,342,556 B1 | 1/2002 | Batdorf et al. | |
| 6,352,583 B1 | 3/2002 | Goettsche et al. | |
| 6,471,969 B1 | 10/2002 | Schlachter et al. | |
| 6,471,976 B1 | 10/2002 | Taylor et al. | |
| 6,475,631 B1 | 11/2002 | Yamamoto et al. | |
| 6,482,814 B1 | 11/2002 | Bath et al. | |
| 6,485,790 B2 | 11/2002 | Walker et al. | |
| 6,503,306 B1 | 1/2003 | Watkins | |
| 6,514,512 B1 | 2/2003 | Puterka et al. | |
| 6,521,288 B2 | 2/2003 | Laks et al. | |
| 6,537,670 B1 | 3/2003 | Sassi | |
| 6,541,038 B1 | 4/2003 | Tanaka et al. | |
| 6,558,685 B1 | 5/2003 | Kober et al. | |
| 6,572,788 B2 | 6/2003 | Walker | |
| 6,576,661 B1 | 6/2003 | Bruck et al. | |
| 6,579,354 B1 | 6/2003 | West | |
| 6,585,989 B2 | 7/2003 | Herbst et al. | |
| 6,593,260 B2 | 7/2003 | Nomura | |
| 6,596,246 B2 | 7/2003 | Huato et al. | |
| 6,646,147 B2 | 11/2003 | Richardson et al. | |
| 6,686,056 B2 | 2/2004 | Roos et al. | |
| 6,689,731 B2 | 2/2004 | Esselborn et al. | |
| 6,699,818 B1 | 3/2004 | Walter et al. | |
| 6,700,006 B2 | 3/2004 | Thames et al. | |
| 6,753,035 B2 | 6/2004 | Laks et al. | |
| 6,770,674 B1 | 8/2004 | Young | |
| 6,830,822 B2 | 12/2004 | Yadav | |
| 6,843,837 B2 | 1/2005 | Zhang et al. | |
| 6,849,276 B1 | 2/2005 | Dufau et al. | |
| 6,867,250 B1 | 3/2005 | Gupta et al. | |
| 6,887,400 B1 | 5/2005 | Wei et al. | |
| 6,905,531 B2 | 6/2005 | Richardson et al. | |
| 6,905,532 B2 | 6/2005 | Richardson et al. | |
| 7,105,136 B2 | 9/2006 | Ploss et al. | |
| 7,238,654 B2 | 7/2007 | Hodge et al. | |
| 7,316,738 B2 | 1/2008 | Richardson et al. | |
| 7,426,948 B2 | 9/2008 | Richardson et al. | |
| 7,449,130 B2 | 11/2008 | Lloyd et al. | |
| 7,674,481 B2 | 3/2010 | Leach et al. | |
| 8,158,208 B2 | 4/2012 | Richardson et al. | |
| 2001/0021711 A1 | 9/2001 | Beilfuss et al. | |
| 2001/0051175 A1 | 12/2001 | Strom et al. | |
| 2002/0003179 A1 | 1/2002 | Verhoff et al. | |
| 2002/0047058 A1 | 4/2002 | Verhoff et al. | |
| 2002/0051892 A1 * | 5/2002 | Laks | A01N 25/12 428/541 |
| 2002/0055046 A1 | 5/2002 | Ono et al. | |
| 2002/0110692 A1 | 8/2002 | Suzuki et al. | |

(56) References Cited

U.S. PATENT DOCUMENTS

| | | |
|---|---|---|
| 2002/0126367 A1 | 9/2002 | Daisey, Jr. et al. |
| 2003/0010956 A1 | 1/2003 | Las et al. |
| 2003/0013799 A1 | 1/2003 | Crooks et al. |
| 2003/0017565 A1 | 1/2003 | Echigo et al. |
| 2003/0040569 A1 | 2/2003 | Curry et al. |
| 2003/0060504 A1 | 3/2003 | Yoshida et al. |
| 2003/0077219 A1 | 4/2003 | Ploss et al. |
| 2003/0086979 A1 | 5/2003 | Ghosh |
| 2003/0108759 A1 | 6/2003 | Roos et al. |
| 2003/0127023 A1 | 7/2003 | Grandidier et al. |
| 2003/0170317 A1 | 9/2003 | Curzon et al. |
| 2004/0024099 A1 | 2/2004 | Narayanan et al. |
| 2004/0050298 A1 | 3/2004 | Giger et al. |
| 2004/0051084 A1 | 3/2004 | Wessling et al. |
| 2004/0063847 A1 | 4/2004 | Curry et al. |
| 2004/0176477 A1 | 9/2004 | Davison et al. |
| 2004/0258767 A1 | 12/2004 | Leach et al. |
| 2004/0258768 A1 | 12/2004 | Richardson et al. |
| 2004/0258838 A1 | 12/2004 | Richardson et al. |
| 2005/0013939 A1 | 1/2005 | Vinden et al. |
| 2005/0107467 A1 | 5/2005 | Richardson |
| 2005/0118280 A1 | 6/2005 | Leach et al. |
| 2005/0130866 A1 | 6/2005 | Richardson et al. |
| 2005/0152994 A1 | 7/2005 | Leach et al. |
| 2005/0182152 A1 | 8/2005 | Nonninger et al. |
| 2005/0249812 A1 | 11/2005 | Leach et al. |
| 2005/0252408 A1 | 11/2005 | Richardson et al. |
| 2005/0255251 A1 | 11/2005 | Hodge et al. |
| 2005/0256026 A1 | 11/2005 | Hodge et al. |
| 2005/0265893 A1 | 12/2005 | Leach et al. |
| 2006/0062926 A1 | 3/2006 | Richardson et al. |
| 2006/0075921 A1 | 4/2006 | Richardson et al. |
| 2006/0075923 A1 | 4/2006 | Richardson |
| 2006/0078686 A1 | 4/2006 | Hodge et al. |
| 2006/0086284 A1 | 4/2006 | Zhang et al. |
| 2006/0086841 A1 | 4/2006 | Richardson et al. |
| 2006/0112850 A1 | 6/2006 | Zhang et al. |
| 2006/0147632 A1 | 7/2006 | Zhang et al. |
| 2006/0257578 A1 | 11/2006 | Zhang et al. |
| 2006/0288904 A1 | 12/2006 | Leach et al. |
| 2007/0021385 A1 | 1/2007 | Zhang et al. |
| 2007/0131136 A1 | 6/2007 | Zhang et al. |
| 2007/0193473 A1 | 8/2007 | Zhang et al. |
| 2007/0259016 A1 | 11/2007 | Hodge et al. |
| 2008/0199525 A1 | 8/2008 | Leach et al. |
| 2008/0199535 A1 | 8/2008 | Taylor et al. |
| 2008/0210121 A1 | 9/2008 | Zhang et al. |
| 2008/0213608 A1 | 9/2008 | Richardson et al. |
| 2008/0260841 A1 | 10/2008 | Leach et al. |
| 2008/0286380 A1 | 11/2008 | Zhang et al. |
| 2009/0028917 A1 | 1/2009 | Leach et al. |
| 2009/0035564 A1 | 2/2009 | Leach et al. |
| 2009/0092683 A1 | 4/2009 | Leach et al. |
| 2009/0143478 A1 | 6/2009 | Richardson et al. |
| 2009/0280185 A1 | 11/2009 | Richardson et al. |

FOREIGN PATENT DOCUMENTS

| | | |
|---|---|---|
| CA | 2103470 A1 | 8/1994 |
| CA | 2251534 A1 | 10/1997 |
| DE | 2531895 A1 | 2/1977 |
| DE | 1531868 U | 11/1978 |
| DE | 3542441 A1 | 6/1987 |
| DE | 3930687 A1 | 4/1991 |
| DE | 4112652 A1 | 10/1992 |
| EP | 0173964 A2 | 3/1986 |
| EP | 0256427 A2 | 2/1988 |
| EP | 0472973 A1 | 3/1992 |
| EP | 0499299 A2 | 8/1992 |
| EP | 0577952 A1 | 1/1994 |
| EP | 1 034 903 A1 * | 9/2000 |
| EP | 1034903 A1 | 9/2000 |
| EP | 1649749 A1 | 4/2006 |
| GB | 222268 A | 10/1924 |
| GB | 812408 A | 4/1959 |
| GB | 822869 A | 11/1959 |
| GB | 1491330 A | 11/1977 |
| GB | 1531868 A | 11/1978 |
| JP | S60-89422 | 4/1985 |
| JP | 60-155403 A | 8/1985 |
| JP | 61-244502 | 10/1986 |
| JP | 61-246002 A | 11/1986 |
| JP | S62-39201 | 2/1987 |
| JP | S62-116102 | 5/1987 |
| JP | S64-026401 A | 1/1989 |
| JP | 8-183010 A | 7/1996 |
| JP | 10-272610 A | 10/1998 |
| JP | 2000-102907 A | 4/2000 |
| JP | 2000-141316 A | 5/2000 |
| JP | 2001-121512 A | 5/2001 |
| JP | 2003/266406 A | 9/2003 |
| NZ | 225428 A | 3/1991 |
| NZ | 280716 A | 2/1999 |
| NZ | 304884 A | 3/1999 |
| PL | 169344 | 5/1994 |
| SE | 379167 B | 9/1975 |
| SU | 0642166 A1 | 1/1979 |
| WO | WO-85/00040 A1 | 1/1985 |
| WO | WO-87/04696 A1 | 8/1987 |
| WO | WO-92/19429 A1 | 11/1992 |
| WO | WO-95/27600 A1 | 10/1995 |
| WO | WO-98/05206 A1 | 2/1998 |
| WO | WO 98/05206 A1 * | 2/1998 |
| WO | WO-99/55505 A1 | 11/1999 |
| WO | WO-00/05955 A1 | 2/2000 |
| WO | WO-00/24259 A1 | 5/2000 |
| WO | WO-00/24528 A1 | 5/2000 |
| WO | WO-00/60940 A1 | 10/2000 |
| WO | WO-00/78281 A1 | 12/2000 |
| WO | WO-01/91925 A1 | 12/2001 |
| WO | WO 02/00196 A1 * | 1/2002 |
| WO | WO-02/00196 A2 | 1/2002 |
| WO | WO-02/06417 A1 | 1/2002 |
| WO | WO-03/025303 A1 | 3/2003 |
| WO | WO-03/103392 A1 | 12/2003 |
| WO | WO-2004/091875 A2 | 10/2004 |
| WO | WO-2005/007368 A2 | 1/2005 |
| WO | WO-2005/104841 A1 | 11/2005 |
| WO | WO-2005/110692 A2 | 11/2005 |
| WO | WO-2005/115704 A2 | 12/2005 |
| WO | WO-2006/042128 A2 | 4/2006 |
| WO | WO-2006/042129 A1 | 4/2006 |
| WO | WO-2006/044218 A2 | 4/2006 |

OTHER PUBLICATIONS

Backman, P.A., et al., "The Effects of Particle Size and Distribution on Performance of the Fungicide Chlorothalonil, Phytopathology," St. Paul, MD, US, vol. 66, No. 10, 1 Jan. 1, 1976, pp. 1242-1245, XP009062911.
Supplementary European Search Report for PCT/US2005/016503 dated Feb. 2, 2009.
Supplementary European Search Report for PCT/US2005/037303 dated Feb. 5, 2009.
Koch, C.C., Synthesis of Nanostructured Materials by Mechanical Milling: Problems and Opportunities, NanoStructured Materials, vol. 9, pp. 13-22, 1997.
American Wood-Preservers' Association Standard E7-07, "Standard Method of Evaluating Preservatives by Filed Tests with Stakes," 2006.
American Wood-Preservers' Association Standard E10-01, "Standard Method of Testing Wood Preservatives by Laboratory Soil-Block Cultures," 2005.
The Merck Index (12th Ed. 1996) Merck & Co., Inc.
Davis, Food Storage and Preservative-Treated Wood, Alaska Science Forum (Mar. 10, 1980) [online][retrieved on Nov. 10, 2008].. URL:http://www.gi.alaska.edu/ScienceForum/ASF3/380.htm/.
STN online, file SCISEARCH, Acc. No. 1993:540390 (Siegfried, Comparative Toxicity of Pyrethoid Insecticides to Terrestial and Aquatic Insects, Environmental Toxicology and Chemistry (1993), vol. 12, No. 9, pp. 1683-1689.

(56) References Cited

OTHER PUBLICATIONS

Superior Court of New Jersey, Decision After Trial, *Phibro-Tech, Inc.* v. *Osmose Holdings, Inc.*, Jun. 25, 2007.
Superior Court of New Jersey, Chancery Division, Final Judgment, *Phibro-Tech, Inc.* v. *Osmose Holdings, Inc.*, Osmose, Inc., Aug. 14, 2007.
Liu, Y., et al., Use of Nanoparticles for the Controlled Release of Biocides in Pressure-Treated Solid Wood, Polymer Preprints 38(2), 1997, pp. 624-625.
Liu, Y.. et al., Michigan Technical Univ., Dept. of Chemistry, Houghton, MI, Use of Polymeric Nanoparticles for Controlled Release of Biocides in Solid Wood, Materials Research Society Symposium Proceedings Series; 1998, vol. 550, Abstract GG3.4.
Liu, Y., et al., "Use of Polymer Nanoparticles as Carriers for the Controlled release of Biocides in Solid Wood". Ph.D. Dissertation of Yong Liu; Michigan Technological University, Houghton, MI, 1999.
Liu, Y., et al., Use of Nanoparticles for Controlled Release of Biocides in Solid Wood, Journal of Applied Polymer Science, vol. 79, 2001, pp. 458-465.
Lide, Characteristics of Particles and Particles Dispersoids Handbook of Chemistry and Physics, 75th edition; 1994, Florida: CRC Press, pp. 15-38.
Shaw, www.fda.gov/ohmrms/dockets/ac/01/slides/3763s2_09_shaw.ppt; 2001.
The Australian Clay Minerals Society, "About Clays," (http://www.clays.org.au/mins.htm) printed website on Nov. 18, 2011.
Hawley's Condensed Chemical Disctionary, 14th Edition, John Wiley & Son, Inc., 2001, p. 86.
JP Published Unexamined Patent Application No. S61-246002 (Nov. 1, 1986).
JP Published Unexamined Patent Application No. S61-244502 (Oct. 30, 1986).
Schultz, T.P., et al., "A Brief Overview of Non-Arsenical Wood Preservative," American Chemical Society, Chapter 26, pp. 420-429, 2003.
S. E. A. McCallan, The Nature of the Fungicidal Action of Copper and Sulfur, The Botanical Review, pp. 629-643, Aug. 30, 1948.
M. Humar et al., "Influence of Moisture Content on EPR Parameters of Copper in Impregnated Wood," Holz als Roh-Und Werkstoff 59 (2001) 254-255.
M. Humar et al., Changes of the pH of impregnated Wood During Exposure to Wood-Rotting Fungi, Holz als Roh-und Werkstoff 59 (2001) 288-293.
A. Pizzi, "A New Approach to Non-Toxic, Wild-Spectrum, Ground-Contact Wood Preservatives. Pat I. Approach and Reaction Mechanisms," Holzforschung 47 (1993) 253-260.
A. Pizzi, "A New Approach to Non-Toxic, Wild-Spectrum, Ground-Contact Wood Preservatives. Pat II. Accelerated and Long-term Field Tests," Holzforschung 47 (1993) 343-348.
Stan Lebow, et al., "Fixation Effects on the Release of Copper, Chromium and Arsenic From CCA-C Treated Marine Piles, Report Prepared for American Wood-Preservers' Association Subcommitte P-3," Piles, Aug. 1999, pp. 168-174.
Izabela Ratajczak, et al., "Fixation of Copper (II)-Protein Formulation in Wood: Part 1. Influence of Tannic Acid on Fixation of Copper in Wood," Holzforschung, vol. 62, pp. 294-299, 2008.
S. N. Kartal, et al., "Do the Unique Properties of Nanometals Affect Leachability or Efficacy Against Fungi and Termines?" International Biodeterioration & Biodegradation 63 (2009) 490-495.
H. Kubel, et al., The Chemistry and Kinetic Behavior of Cu—Cr—As/B Wood Preservatives—Part 5. Reactions of CCB and Cellulose, Lignin and their Simple Model Compounds, Holzforschung und Holzverwertung 34 (1982) 4, pp. 75-83.
A. Pizzi, et al., The Chemistry and Kinetic Behavior of Cu—Cr—AS/B Wood Preservatives—Part 6. Fixation of CCB in Wood and Physical and Chemical Comparison of CCB and CCA, Holzforschung and Holzverwertung 34 (1982) 5, pp. 80-86.
Raul A. Wapnir, Copper Absorption and Bioavailability, Am J Clin Nutr. 1998; 67 (suppl.): 1054S-60S.

Gadi Borkow, et al., Copper As a Biocidal Tool, Proceedings, ninety-Fifth Annual Meeting of the American Wood Preservers' Association, vol. 95, May 16-19, 1999.
H. S. Rathore, et al., Fungicide and Herbicide Residues in Water, Handbook of Water Analysis. pp. 608-654, Handbook of Water Analysis, 2000.
T.C. Crusberg, et al., Biomineralization of Heavy Metals, pp. 409-417, 2004.
5.1 Inorganic Fungicides—5.1.1 Metal Salts, Pesticide Chemistry, pp. 272-486, 1988.
R. Thompson, CBE, The Chemistry of Wood Preservation, Feb. 28-Mar. 1, 1991.
H. M. Barnes, et al., The Impact of Test Site and Oil Content on the Performance of Pentachlorophenol-Treated Wood, Forest Products Journal, vol. 56, No. 5, pp. 43-47, May 2006.
J.J. Morrell, Wood Pole Maintenance Manual (1996 Edition), Research Contribution 15, Oct. 1996, p. 22.
Helmuth Rech, "Location of Pentachlorophenol by Electron Microscopy and Other Techniques in Cellon Treated Douglas-Fir," Forest Products J. 21/1, pp. 38-43, Jan. 1971.
M. Humar, et al., Effect of Oxalix, Acetic Acid, and Ammonia on Leaching of Cr and Cu From Preserved Wood, Wood Sci Technol 37 (2004) 463-473.
Cui, F. and Archer, K. J., "Treatment of lumber with preservative/water repellent emulsions—The significance of shear stability on penetration," The International Re-search Group on Wood Preservation, IRG/WP 97-20124, Paper prepared for the 28th Annual Meeting, Whistler, British Columbia, Canada (May 25-30, 1997).
Feist and Mraz, Forest Products Lab Madison Wis., Wood Finishing: Water Repellents and Water-Repellent Preservatives. Revision, Report No. FSRN-FPL-0124-Rev (NTIS 1978).
Fojutowski, A.; Lewandowski, O., Zesz. Probl. Postepow Nauk Roln. No. 209: 197-204 (1978).
Hamilton, R.L. and Cosse, O. K., "Thermal Conductivity of Heterogenous Two-Component Systems," Ind. & Engr. Chem. Fund., 1, 187-191 (1962).
Laks, et al., "Polymer Nanoparticles as a Carrier System for Wood Preservatives," PowerPoint Presentation to Rohm & Haas under confidentiality agreement, Oct. 30, 1998 (even-numbered pages not available).
Nanotechnology in brief, Feb. 20, 2004, available at http://nanotechweb.org/articles/news/3/2/12/1.
Nasibulin Albert G., Ahonen, P. Petri, Richard, Richard, Olivier, Esko I, "Copper and Cooper Oxide Nanoparticle Formation by Chemical Vapor Nucleation From Copper (II) Acetylacetonate," Journal of Nanoparticles Research 3(5-6): 383-398 (2001).
Panshin AJ and De Zeeuw, Carl, Textbook of Wood Technology, 4th ed. pp. 112-113 (1980).
Supplementary European Search Report dated Apr. 21, 2009 for PCT/US2005/035946.
Bailey, Irving W., "The Preservative Treatment of Wood, II. The Structure of the Pit Membranes in the Tracheids of Conifers and their Relation to the Penetration Gases, Liquids, and Finely Divided Solids into Green and Seasoned Wood," Forest Quarterly, 11:12-20, p. 15 (1913).
Merriam-Webster's Collegiate Dictionary, 10th ed., 1993.
The Copper Champs! Unique Copper Hydroxide Formulations (Brochure). Nufarm Americas Inc. (2002).
Zahora, A. R. and Rector, C.M., "Water Repellent Additives for Pressure Treatments," Proceedings of the Eleventh Annual Meeting of the Canadian Wood Preservation Association, Toronto, Ontario, 11:22-41 (Nov. 6 and 7, 1990).
"Defendants' Answer to Plaintiff's Amended Complaint and Defendants' Counterclaims," Jun. 21, 2010, *Osmose, Inc.* v. *Arch Chemicals, et al.*, USDC, Eastern District of VA, Norfolk Division Case No. C.A. No. 2:10 cv 108-JBF/FBS.
"Osmose's Answer to Defendants' Counterclaims," *Osmose, Inc.* v. *Arch Chemicals, et al.*, USDC, Eastern District of VA, Norfolk Division Case No. C.A. No. 2:10 cv 108-JBF/FBS.
"Defendants' Supplemental Response to Interrogatory No. 12 and its Subparts," *Osmose, Inc.* v. *Arch Chemicals, et al.*, USDC, Eastern District of VA, Norfolk Division Case No. C.A. No. 2:10 cv 108-JBF.

(56) References Cited

OTHER PUBLICATIONS

Notice of Opposition to a European Patent (Application No. EP04776802.3/Patent No. EP1651401), filed by Dr. David Elsy on Apr. 21, 2010.
Statement of Grounds and Particulars filed by Arch Wood Protection Pty Ltd. with the Commissioner of Patents on Dec. 18, 2009, in the Matter of Australian Patent Application No. 2004230950 in the Name of Osmose, Inc.
Rudd, et al. "The Influence of Ultraviolet Illumination on the Passive Behavior of Zinc," Journal of the Electrochemical Society, 147 (4) p. 1401-1407, 2000.
American Wood-Preservers' Association (AWPA) Standard A3-00, 2003.
Proceedings of the Fourth International Congress Pesticide Chemistry (IUPAC), Article VII-23, 1978.
Statutory Declaration of Dr. Robin Nicholas Wakeling, in the matter of Australian Patent Acceptance No. 2004230950 and Opposition thereto, dated Sep. 20, 2010.
Hungarian Search Report dated Jul. 15, 2010 for Singaporean Patent Application No. 200717645-6.
Australian Patent Office Examination Report dated Jun. 1, 2010 for Singaporean Patent Application No. 200717652-2.
Notice of Opposition to Grant of Patent (Section 21) (Application No. 542889) filed by Mattersmiths Holdings Limited on Jun. 22, 2010.
Ernest W. Flick, "Fungicides, Biocides and Preservatives for Industrial and Agricultural Applications," 1987, Noyes Publication, p. 184.
American Wood-Preservers' Association (AWPA) Standard E-11-97, pp. 1-3, 2003.
Opinion and Order dated Jan. 28, 2011, *Osmose, Inc.* v. *Arch Chemicals, Inc., et al.*, Civil Action No. 2:10 cv 108.
Expert Report of Dr. Frank Beall, Ph.d. Concerning the Invalidity of U.S. Pat. No. 7,674,481, U.S. District Court for the Eastern District of Virginia, Norfolk Division, Civil Action No. 2:10 cv 108.
Supplemental Expert Report of Dr. Frank Beall, Ph.D. Concerning the Invalidity of U.S. Pat. No. 7,674,481, Feb. 11, 2011, USDC Eastern District of Virginia, Norfolk Division, Civil Action No. 2:10cv108.
Rebuttal Expert Report of John Ruddick, Feb. 22, 2010, USDC Eastern District of Virginia, Norfolk Division, Civil Action No. 2:10cv108. (Redacted).
American Wood Preservers' Association (AWPA) Standard E10-06, "Standard Method of Testing Wood Preservatives by Laboratory Soil-Block Cultures," 2007.
American Wood Preservers' Association (AWPA) Standard E10-09, "Standard Method of Testing Wood Perseverative by Laboratory Solid-Block Cultures," 2010.
American Wood Preservers' Association (AWPA) Standard E11-06, "Standard Method of Determining the Leachability of Wood Preservatives," 2007.
American Wood Preservers' Association (AWPA) Standard E22-09, "Standard Accelerated Laboratory Method for Testing the Efficacy of Preservatives Against Wood Decay Fungi Using Compression Strength," 2010.
ASTM D5664, "Standard Test Method for Evaluating the Effects of Fire-Retardant Treatments and Elevated Temperatures on Strength Properties of Fire Retardant Treated Lumber," 2002.
"Preservation of Timber with Zinc Chloride by the Steep Process," Technical Notes, Forest Products Laboratory, U.S. Forest Service.
Freeman, Mike et al. "A Comprehensive Review of Copper-Based Wood Preservatives," Forest Products Journal, vol. 58, No. 11, pp. 6-27, Nov. 2008.
Stirling, Rod, et al., "Micro-Distribution of Micronized Copper in Southern Pine," The International Research Group on Wood Protection, 39th Annual Meeting, May 25-28, 2008.
The Federal Circuit Bar Association Model Patent Jury Instructions.
Liese, W., "Fine Structure of Bordered Pits in Softwoods" Cellular Ultrastructure of Woody Plants, pp. 271-290, 1995.
Graph, "Fine Structure of Bordered Pits in Softwoods."
Response to Office Action by Patent Owner in inter Partes Reexamination Under 37 CFR § 1.945, USPTO Reexamination Control No. 95/001,418, filed by Osmose, Inc., Dec. 21, 2010.
Third Party Comments after Patent Owner Response, USPTO Reexamination Control No. 95/001,418, filed by Arch Wood Protection, Inc., Jan. 20, 2011.
Liu, Y., et al., "Use of Nanoparticles for the Controlled Release of Biocides in Pressure-treated Solid Wood"; Presentation at the American Chemical Society, Las Vegas, Oct. 1997.
Amended Notice of Opposition to Grant of Patent (Section 21) and Statement of Case (Application No. 542889) filed by Mattersmiths Holdings Limited on Aug. 23, 2010; and Notice of Opposition to Grant of Patent (Section 21) (Application No. 542889) filed my Mattersmiths Holdings Limited on Jun. 22, 2010.
Request for Inter Partes Reexamination of U.S. Pat. No. 7,674,481 filed with the United States Patent and Trademark Office by Arch Wood Protection, Inc. on Aug. 13, 2010 and a draft of the Request.
Patent Owner's Response Under 37 CFR 1.951(a) to the Action Closing Prosecution in Inter Partes Reexamination Control No. 95/001,418. May 27, 2011.
Declaration of Dr. John N.R. Ruddick Under 37 CFR 1.132, in Inter Partes Reexamination Control No. 95/001,418. May 26, 2011.
First Office Action issued Oct. 21, 2010 in Inter Partes Reexamination Control No. 95/001,418.
Action Closing Prosecution issued Apr. 29, 2011 in Inter Partes Reexamination Control No. 95/001,418.
Dev et al., "Termite Resistance and Permanency Tests on Zinc-Borate—An Environmental Friendly Preservative," J. Timb. Dev. Assoc. (India) vol. XLIII, No. 2, Apr. 1997.
Laks et al., "Anti-sapstain efficacy of borates against *Aureobasidium pullulans*," Forest Products Journal 43(1): 33-34 (1993).
Shchigol, "Some Properties of Zinc and Cadmium Borates," Russian Journal of Inorganic Chemistry, 913-915 (1959).
Tsunoda, "Effects of zinc borate on the properties of medium density fiberboard. (Composites and Manufactured Products)," Forest Products Journal (Nov. 1, 2002).
Wang et al., "Treatability and durability of heartwood," in Ritter et al., eds., National Conference on Wood Transportation Structures, Oct. 23-25, 1995, Madison WI; Gen. Tech. Rep. FPL-GTR-94, Madison, WI: U.S.D.A. Forest Service, Forest Products Laboratory pp. 252-260 (1996).
Dev et al. "Termite Resistance and Permanency Tests on Zinc-Borate—An Environmental Friendly Preservative," Timb. Dev. Assoc. (India) vol. XLIII, No. 2, Apr. 1997.
Laks et al. "Anti-Sapstain efficacy of borates against *Aureobasidium pullulans*," Forest Products Journal 43(1):33-34 (1993).
Shchiol "Some Properties of Zinc and Cadmium Borates" Russian Journal of Inorganic Chemistry, 913-915 (1959).
Tsunoda "Effects of zinc borate on the properties of medium density fiberboard. (Composites and Manufactured Products)." Forest Products Journal (Nov. 1, 2002).
Wang JZ, DeGroot R "Treatability and durability of heartwood" In: Ritter, M.A.; Duwadi, S.R.; Lee, P.Dh., ed(s). National conference on wood transportation structures: Oct. 23-25, 1996; Madison, WI. Gen. Tech. Rep. FPL-GTR-94, Madison, WI: U.S. Department of Agriculture, Forest Service, Forest Products Laboratory pp. 252-260 (1996).
Liu, et al., "Controlled Release of Biocides in Solid Wood. I. Efficacy Against Brown Rot Wood Decay Fungus," Journal of Applied Polymer Science, 2002, vol. 86, pp. 596-607.
Lewis Sr., R. J., "Antineoplastic," Hawley's Condensed Chemical Disctionary, 14th Edition, John Wiley & Son, Inc., 2001, p. 86.
Patent Trial and Appeal Board Decision on Appeal in Reexamination Control No. 95/001,418, Jan. 28, 2013.
Liese, W., "Fine Structure of Bordered Pits in Softwoods" Cellular Ultrastructure of Woody Plants, pp. 271-290, 1965.
Liese, W., "Fine Structure of Bordered Pits in Softwoods" Cellular Ultrastructure of Woody Plants, pp. 285 (Graph), 1965.

\* cited by examiner

Milled

Unmilled

PARTICULATE WOOD PRESERVATIVE AND METHOD FOR PRODUCING SAME

RELATED APPLICATIONS

This application is a continuation application of U.S. application Ser. No. 13/446,373, filed Apr. 13, 2012, now U.S. Pat. No. 8,722,198 B2, which is a continuation application of U.S. application Ser. No. 12/209,653, filed Sep. 12, 2008, now U.S. Pat. No. 8,158,208 B2 which is a continuation application of U.S. application Ser. No. 10/961,206, filed Oct. 12, 2004, now abandoned, which claims the benefit of U.S. Provisional Application No. 60/571,535, filed May 17, 2004, and U.S. Provisional Application No. 60/616,646, filed Oct. 8, 2004, all of which are herein incorporated by reference in their entireties.

FIELD OF THE INVENTION

The present invention relates to particulate-based biocidal compositions, particularly wood preservatives comprising particles including one or more copper compounds. More particularly, the invention relates to a method of manufacture of particulate-based biocidal compositions capable of being injected into wood, the biocidal compositions, methods of preserving wood using the compositions, and wood treated with the compositions of this invention.

BACKGROUND OF THE INVENTION

Preservatives are used to treat wood to resist insect attack and decay. The commercially used preservatives are separated into three basic categories, based primarily on the mode of application, into waterborne, creosote, and oil borne preservatives. Waterborne preservatives include chromated copper arsenate (CCA), ammoniacal copper quat, ammoniacal copper zinc arsenate, and ammoniacal copper arsenate. Wood treated with these chemicals sometimes turn green or grey-green because of a chemical reaction between copper in the preservative and the sun's ultraviolet rays. The preservatives leach into the soil over time, but the copper amines leach from wood at rates several times those observed for CCA.

The primary preserved wood product has historically been southern pine lumber treated with chromated copper arsenate (CCA). Most of this treated lumber was used for decks, fencing and landscape timbers. There has recently been raised concerns about the safety and health effects of CCA as a wood preservative, primarily relating to the arsenic content but also to the chromium content. In 2003/2004, due in part to regulatory guidelines and to concerns about safety, there has been a substantial cessation of use of CCA-treated products. A new generation of copper containing wood preservatives use a form of copper that is soluble. Known preservatives include copper alkanolamine complexes, copper polyaspartic acid complex, alkaline copper quaternary, copper azole, copper boron azole, copper bis(dimethyldithiocarbamate), ammoniacal copper citrate, copper citrate, and the copper ethanolamine carbonate. In practice the principal criteria for commercial acceptance, assuming treatment efficacy, is cost. Of the many copper-amine compositions listed above, only the copper ethanolamine carbonate and ammoniacal copper are in widespread use. There are several problems with these new copper-amine-containing preservatives.

The soluble copper containing wood preservatives are very leachable, compared to CCA. This leaching is of concern for at least two reasons: 1) removal of the copper portion of the pesticide from the wood by leaching will compromise the long term efficacy of the formulation, and 2) the leached copper causes concern that the environment will be contaminated. Copper is extremely toxic to certain fish at sub-part per million levels. One study reported the Synthetic Precipitation Leaching Procedure gave the leachate from CCA-treated wood contained a baseline concentration of about 4 mg copper per liter; leachate from copper (ammonium) boron azole-treated wood contained seven times the baseline; leachate from copper bis(dimethyldithiocarbamate) treated wood had twice the baseline concentration; leachate from alkaline copper quaternary treated wood had over seven times the baseline concentration; and leachate from copper citrate treated wood had over fifteen times the baseline concentration. Copper leaching is such a problem that some states do not allow use of wood treated with the soluble copper containing wood preservatives near waterways.

The commercial soluble copper containing wood preservatives cause increased metal corrosion, for example of nails within the wood. Preserved wood products are often used in load-bearing out-door structures such as decks. Traditional fastening material, including aluminum and standard galvanized fittings, are not suitable for use with wood treated with these new preservatives. Many regions are now specifying that hardware, e.g., fittings, nails, screws, and fasteners, be either galvanized with 1.85 ounces zinc per square foot (a G-185 coating) or require Type 304 stainless steel.

Further, the copper-containing portion of the treatment is not protective against some biological species, and these soluble copper containing wood preservatives require higher copper loading, a second organic biocide, or both to be effective. Indeed, we believe the amines from the copper-amine complex encourage the growth of molds, particularly sapstain molds.

Another concern with soluble copper preservative products generally is that most preservative materials are manufactured at one of several central locations but are used in disparate areas and must be shipped, sometimes substantial distances. The cost of providing and transporting the liquid carrier for these soluble products can be considerable, and the likelihood of an extreme biological impact on fish is very high if transported soluble copper wood preservative material is spilled or accidentally released near a waterway.

Finally, the cost of the amine—between three and 4 moles of amine are required to solubilize a mole of copper) is very high. This application proposes wood preservatives which solve each of these problems.

SUMMARY OF THE INVENTION

The principal aspect of the invention is sparingly soluble or substantially insoluble, biocidal particulates adapted to be incorporated into as a preservative treatment into wood and wood products. The biocide particulates preferably contain one or more sparingly soluble, copper-, zinc- and/or tin-containing particulates. Optionally the biocidal particulates can comprise solid, substantially insoluble organic biocides. Optionally, one or more of the biocidal particulates can further comprise a permeable coating of a substantially insoluble organic biocide. The biocide particulates of the current invention are also advantageously incorporated in nonfouling paints and coatings. Additionally, the biocide particulates when used in foliar applications on crops provides an efficacious treatment that is more resistant to rain, and the amount of the biocide may be reduced compared to prior art formulations having larger mean particle sizes and wider particle size distributions.

A first embodiment of this invention is an effective, long-lasting, environmentally responsible, non-staining/coloring, inexpensive, non-corrosion-inducing, injectable, sparingly soluble copper-salt-containing particulate preservative treatment for wood and wood products that is substantially free of hazardous material. As used herein the term injectable means readily injectable into Southern Pine wood using conditions standard in the industry (e.g., partial vacuum and up to 120 psig) for a distance of at least several inches into the wood. A second embodiment of this invention is an effective, long-lasting, inexpensive, non-corrosion-inducing, micron- to sub-micron-sized, sparingly soluble copper-salt-containing particulates for use in non-fouling paints and coatings, and for use in foliar applications.

A third embodiment of this invention is an effective, long-lasting, environmentally responsible, non-staining/coloring, inexpensive, non-corrosion-inducing, injectable, sparingly soluble zinc-salt-containing particulate preservative treatment for wood and wood products that is substantially free of hazardous material. A fourth embodiment of this invention is an effective, long-lasting, inexpensive, non-corrosion-inducing, micron- to sub-micron-sized, sparingly soluble zinc-salt-containing particulates for use in non-fouling paints and coatings, and for use in foliar applications.

Another embodiment of this invention is an effective, long-lasting, environmentally responsible, non-staining/coloring, inexpensive, non-corrosion-inducing, injectable, sparingly soluble tin-salt-containing particulate preservative treatment for wood and wood products that is substantially free of hazardous material.

A fifth embodiment of this invention is an effective, long-lasting, environmentally responsible, non-staining/coloring, inexpensive, non-corrosion-inducing, injectable, substantially insoluble solid organic biocide-containing particulate preservative treatment for wood and wood products that is substantially free of hazardous material. A sixth embodiment of this invention is an effective, long-lasting, inexpensive, non-corrosion-inducing, sub-micron-sized, substantially insoluble solid organic biocide-containing particulate for use in non-fouling paints and coatings, and for use in foliar applications. As used herein, the term "organic biocide" also includes organometallic biocides. By "substantially insoluble" (or "sparingly soluble" as the term relates to organic biocides), we mean the organic biocide has a solubility in water of less than about 0.1%, and most preferably less than about 0.01%, for example in an amount of between about 0.005 ppm and about 1000 ppm, alternatively between about 0.1 ppm and about 100 ppm or between about 0.01 ppm and about 200 ppm.

The copper-containing particles, the zinc-containing particles, tin-containing particles, and the substantially insoluble solid organic biocide-containing particles can be used independently, but considerable synergy can be achieved by using these in combinations of two or all three. In some embodiments, copper(I) oxide and/or zinc oxide may be used to partially or completely replace the sparingly soluble copper salts and the sparingly soluble zinc salts respectively. Certain copper salts of organic biocidal materials and copper(I) oxide, and also the sparingly soluble copper salts, are generally referred to as copper-containing biocidal compounds. Similar terms are used for zinc compounds.

In a preferred embodiment, the copper-containing particulates comprise sparingly soluble copper salts. Exemplary particles comprise for example copper hydroxide and optionally a copper oxide. At least about 20%, 30%, 50%, or 75% of the weight of the copper-based particles may be composed of the sparingly soluble copper salt. Exemplary copper-containing particles of the invention are sufficiently small to be injectable into the wood. For example, substantially all of the copper-containing particles may be sized to occupy pores or vesicles of wood. In one embodiment, exemplary wood preservatives comprise copper-containing particles having a size distribution in which at least 50% of particles have a diameter smaller than 0.25 microns, 0.2 microns, or 0.15 microns. That particular characteristic, however, is not determinative on whether or not particles are suitable for injection into wood.

As used herein, particle diameters may be expressed as "$d_{xx}$" where the "xx" is the weight percent (or alternately the volume percent) of that component having a diameter equal to or less than the $d_{xx}$. The $d_{50}$ is the diameter where 50% by weight of the component is in particles having diameters equal to or lower than the $d_{50}$, while just under 50% of the weight of the component is present in particles having a diameter greater than the $d_{50}$. Particle diameter is preferably determined by Stokes Law settling velocities of particles in a fluid, for example with a Model LA 700 or a CAPA™ 700 sold by Horiba and Co. Ltd., or a Sedigraph™ 5100 T manufactured by Micromeritics, Inc., which uses x-ray detection and bases calculations of size on Stoke's Law, to a size down to about 0.2 microns. Smaller sizes are preferably determined by a dynamic light scattering method, preferably with a Coulter™ counter.

In one embodiment, wood or a wood product are impregnated with dispersed copper-containing biocidal particles of the invention. Sparingly soluble copper salts in particles within wood or wood products are less leachable than a dried injected solution of the sparingly soluble copper salts, and is also less leachable than prior art soluble copper-amine preservatives. Preferably, the copper-containing biocidal particles are sufficiently insoluble so as to not be quickly removed by leaching but are sufficiently soluble to exhibit toxicity to primary organisms primarily responsible for the decay of the wood.

Generally, crystalline sparingly soluble salts are preferred because they have lower rates of dissolution than do amorphous salts. However, sparingly soluble amorphous salts are equally effective, and particulates made from amorphous salts can have copper release and copper-leach characteristics similar to those of the substantially crystalline sparingly soluble salts. Any discussion relating to substantially crystalline salts should be considered a preferred variant of the invention, as the same disclosure is generally equally applicable to amorphous sparingly soluble copper salts, or substantially amorphous sparingly soluble copper salts.

A "sparingly soluble" salt as used herein has a $K_{sp}$ in pure water between about $10^{-8}$ to about $10^{-24}$ for salts with only one anion, and from about $10^{-12}$ to about $10^{-27}$ for salts with two anions. Preferred sparingly soluble salts have a $K_{sp}$ between about $10^{-10}$ to about $10^{-21}$. As used herein, preferred sparingly soluble inorganic salts includes salts with a $K_{sp}$ of between about $10^{-12}$ to about $10^{-24}$ for salts with only one anion, and from about $10^{-14}$ to about $10^{-27}$ for salts with two anions. Preferred sparingly soluble copper salts include copper hydroxide, basic copper carbonate, basic copper chloride (copper oxychloride), and basic copper sulfate. The copper-containing particulates can comprise or consist essentially of any sparingly soluble copper salts, including those selected from copper hydroxides; copper carbonates (e.g., "yellow" copper carbonate); basic (or "alkaline") copper carbonate; basic copper phosphate, basic copper phosphosulfate, basic copper sulfates including particularly tribasic copper sulfate; basic copper nitrates; copper oxychlorides (basic copper chlorides); copper borates; basic copper borates; Copper ferricyanate; Copper Fluorosilicate; Copper Thiocyanate; Copper diphosphate or Copper pyrophosphate, Copper Cyanate; and mixtures and combinations thereof. In a preferred embodiment the sparingly soluble copper salts in the copper-containing biocidal particles comprise or consist essentially of one or more copper salts selected from copper hydroxides; copper carbonates, basic copper carbonates; basic copper phosphate, basic copper phosphosulfate, tribasic copper sulfate; copper oxychlorides (basic copper chlorides); basic copper borates, and mixtures thereof. In one embodiment, the particles comprise at least about 20%, 30%, 50%, or 75% of the weight of the any of these sparingly soluble copper salts. The most preferred inorganic copper salts are copper hydroxide and basis copper carbonate.

In another embodiment the copper-containing particulates can comprise or consist essentially of the group consisting of copper oxide, with the proviso that at least one of the biocides is not a copper oxide. Of the copper oxides, $Cu_2O$ is preferred over CuO.

In any of the above the sparingly soluble copper salt can have a substantial amount of one or more of magnesium, zinc, or both, wherein these cations are either dispersed within the sparingly soluble copper composition or be a separate phase within a particulate. In preferred embodiments of the invention, at least some particulates comprise copper hydroxide, basic copper carbonate, or both, having magnesium ions therein. In more preferred embodiments, the copper hydroxide or basic copper carbonate comprises between 6 and 20 parts of magnesium per 100 parts of copper, for example between 9 and 15 parts of magnesium per 100 parts of copper. Alternatively, in another more preferred embodiments, the copper hydroxide comprises between 6 and 20 parts total of magnesium and zinc per 100 parts of copper, for example between 9 and 15 parts total of magnesium and zinc per 100 parts of copper. In some embodiments, the basic copper carbonate comprises between 6 and 20 parts of magnesium per 100 parts of copper, for example between 9 and 15 parts of magnesium per 100 parts of copper, or alternatively between 6 and 20 parts total of magnesium and zinc per 100 parts of copper, for example between 9 and 15 parts total of magnesium and zinc per 100 parts of copper. Alternatively or additionally, in a preferred embodiment, the copper hydroxide and/or basic copper carbonate comprises between about 0.01 and about 5 parts of phosphate per 100 parts of copper, for example between 9 and 15 parts of phosphate per 100 parts of copper.

In another preferred embodiment, slurry alternately or additionally comprises zinc or copper borate particulates, or basic zinc borate, or basic copper borate. As the solubility of copper borate is very pH sensitive, in a preferred embodiment the sparingly soluble copper salts comprise an alkaline material, e.g., copper hydroxide or copper carbonate, to reduce the solubility of the copper borate. If present, the zinc borate loading can range from 0.025% to 0.5%, for example, independent of the copper loading in the wood.

In any of the above-described embodiments, the sparingly soluble copper salt in copper-containing particulates can further comprise the substantially insoluble copper salt, for example copper phosphate, $Cu_3(PO_4)_2$. If there are particulates substantially comprising $Cu_3(PO_4)_2$, copper oxide, or copper 8-quinolinolate, the particulates should be exceedingly small, e.g., less than about 0.07 microns, preferably less than about 0.05 microns, to provide maximum surface area to help dissolution of the particles, and the wood treatment should contain a sparingly soluble copper-salt containing particulates, e.g., basic copper carbonate, basic copper borate, basic copper phosphate, basic copper phosphosulfate, basic copper chloride, tribasic copper sulfate, copper hydroxides, and the like.

The zinc analogs of the above are useful for the zinc-based particulates of the alternate embodiments of the invention. In one embodiment the copper-based particulate material can further comprise one or more sparingly soluble zinc salts selected from zinc hydroxide; zinc oxides; zinc carbonate, basic zinc carbonate, zinc phosphate, basic zinc phosphate, zinc oxychloride; zinc fluoroborate; zinc borate, zinc fluoride, "basic zinc borate" (zinc borate and zinc hydroxide in close proximity), or mixture thereof. Zinc borate, with a solubility product constant in pure water of 5×10-11, is the preferred sparingly soluble zinc salt. Further, if in the presence of a high pH, such as would be provided by zinc hydroxide or zinc carbonate, the solubility is further reduced. The zinc salts may be in a separate salt phase, or may be mixed Cu/Zn salts, or combinations thereof. The zinc may be in the form of particulate zinc oxide. In preferred embodiments the particle comprises at least about 40%, preferably at least about 60%, and more preferably at least about 80% by weight of one or more sparingly soluble copper salts, sparingly soluble zinc salts, or mixtures or combinations thereof.

In one embodiment the particulate product can comprise zinc-containing biocidal particles comprising one or more of crystalline zinc compounds selected from zinc hydroxide; zinc oxides; zinc carbonate; zinc oxychloride; zinc fluoroborate; zinc borate, zinc fluoride, or mixture thereof. The preferred zinc-based material are zinc hydroxide, basic zinc borate, basic zinc carbonate, zinc oxide, or mixture thereof, which may be doped with other cations, e.g., from 0.1 to 10% copper, from 0.1 to 10% magnesium, or both, for example, based on the total weight of the cations. In preferred embodiments the particle comprises at least about 40%, preferably at least about 60%, and more preferably at least about 80% by weight of one or more crystalline zinc compounds.

Synergy is often observed in wood preservatives with organic biocides coupled with biocidal sparingly soluble salts, and this synergy is also seen in foliar applications and in non-fouling paint. It is believed that certain organic biocides are normally long-lasting and very effective against most (but not all) undesired bio-organisms, but are ineffective against and may be subjected to degradation be a few bio-organisms. A principal function of the copper in such a system may be to inhibit growth of those bio-organisms that degrade the organic biocides and/or that are resistant to the organic biocides. The most preferred embodiments of this invention have copper-based particulates and optionally one or more of zinc-based particulates and tin-based particulates, and further comprise between about 0.01% to about 20% by weight of one or more organic biocides, based on the weight of the copper- and zinc-containing materials. In addition, in some embodiments, the particulates form a carrier to carry the organic biocides into the wood and help ensure the biocide is well-distributed throughout the wood. Preferred embodiments of the invention are injectable copper-containing biocidal particles that further comprises one or more organic biocides attached to particulates. In other preferred embodiments, the organic biocides are themselves in injectable particulate form, and are combined with the particulate sparingly soluble metal salts (copper, zinc, or tin) to form an injectable slurry of particulates.

Other aspects of this invention include 1) methods to manufacture the sub-micron particulates having the narrow particle size distributions which are advantageous in foliar applications and antifouling paint applications, and which are required in wood preservative applications; 2) methods of formulating the compositions that comprise the particulates for use in foliar applications, wood preservation, and paint formulations; 3) methods of transporting the particulates; and 5) wood and wood products treated with the particulate preservative treatment compositions. We believe the combination of methods to manufacture injectable particles into wood, as well as our formulations, represent a significant discovery. The slurries of this invention can be essentially unaffected by the use of hard water in the slurry. In contrast, the soluble copper-amine solutions used in the prior art precipitated an objectionable residue of calcium and magnesium carbonates onto the surface of the wood. Injection of the present formulation uses the standard operating procedure that is commonly practiced in the industry. The present formulation reduces and optionally eliminates the nitrogen content of the prior art products; and we believe the nitrogen is associated with the enhanced rate of sapstain growth which presently necessitates the use of expensive sapstain control agents. Removal of the fraction of particles having a diameter greater than 1 micron, accomplished with a component of this technology, also means the slurries are stable—slurry particles settle over the course of days or even weeks, so there is little danger of a slurry settling prior to injection. The sparingly soluble biocidal particles are relatively non-leachable, being comparable with the leach rates associated with the CCA products, and being much lower than the leach rates associated with soluble copper amine wood preservatives. Due to lower leach rates, the wood treated with the preservatives of this invention should be usable underground, near waterways, and also in marine applications. The costs per pound of copper is estimated to be 30% to 50% lower than present copper-MEA-carbonate preservatives. Corrosivity of the product will be less than that associated with the copper-amine preservatives. Freight should be only one third that associated with the copper-amine preservatives.

DESCRIPTION OF THE FIGURES

FIG. 1 shows the face of wood blocks injected with unmilled product (~3 micron copper carbonate) and the face of the wood injected with the milled product (~0.2 micron copper carbonate).

FIG. 2 shows the leaching of copper from treated wood blocks for the various particulate slurries and from two controls (Wolman™ E and CCA).

FIG. 3 shows the penetration of injected particulate copper hydroxide through a cross-section of a block of wood, where the block on the left is untreated, the block in the center was injected with copper salt particles in an amount sufficient to supply 0.25 pounds of copper per cubic foot of wood, and the block on the right was treated the same as the treated center block, and then exposed to a solution of dithio-oxamide, which reacts with copper to show a visible dark stain.

DETAILED DESCRIPTION OF THE INVENTION

Unless otherwise specified, all compositions are given in "percent", where the percent is the percent by weight based on the total weight of the entire component, e.g., of the particle, or to the injectable composition. In the event a composition is defined in "parts" of various components, this is parts by weight wherein the total number of parts in the composition is between 90 and 110.

The term "effective" as it pertains to preservatives means the biocidal particulates are sufficiently distributable through the wood product, and is sufficiently soluble and available so as to provide a bio-active concentration of copper ions in the wood matrix. By "bio-active" we mean the preservative treatment is sufficiently biocidal to one or more of fungus, mold, insects, and other undesired organisms which are normally the target of wood preservatives such that these organisms avoid and/or can not thrive in the treated wood. Too low a solubility (or "release rate"), and the copper is not bioactive. At the same time, the injectable copper-containing particles of this invention is intended to have one or more organic-based biocides incorporated therewith in amounts the same as are currently being used with soluble copper preservatives, and efficacy is based on the combination of the copper (and/or zinc) component in combination with the organic biocides.

By "long-lasting" we mean the preservative treatment has an effective life of at least about 20 years under normal outdoor ground-contact use, for example. Too high a solubility of the particulates, and the biocides and biocidal salts are can be leached out of the wood at too fast a rate. Such fast leaching creates environmental problems, i.e., the leached copper contaminates the environment, and also longevity problems, i.e., so much biocide may be leached from the wood that the remaining treatment can no longer provide a bio-active concentration of copper ions.

Leaching is a function of particle size and the solubility of the sparingly soluble material. Larger size particles have lower leach rates, while particles in a size range from 1 to 10 nanometers under certain circumstances will not have a leach rate much different than that of an injected and dried copper salt solution. In preferred embodiments of this invention, the $d_{50}$ is at least 0.04 microns, meaning at least 50% by weight of the copper-containing particulates have a size greater than 40 nanometers. In more preferred embodiments, the $d_{50}$ is 0.08 microns or greater. In one preferred embodiment, at least 80% by weight of the copper-containing particulates have a size between 0.05 microns and 0.4 microns.

Leaching is not the only mechanism whereby material can be flushed from wood. Because the material is in particulate form, there is a possibility that particulates will be flushed from the wood. Evidence suggests that very small substantially spherical nanoparticles, i.e., spherical particles of size 5 to 20 nanometers, can migrate freely through a wood matrix. However, while said particles are easy to inject, they are also clearly easily transported through wood and would be easily flushed from the wood. These wood preservative treatments would not be long-lasting. Therefore, in preferred embodiments of the invention the material is substantially free of substantially spherical particulates, wherein the particle diameter is less than about 20 nanometers, particularly less than 15 nanometers. By substantially free we mean the $d_{20}$ is greater than 0.02 microns.

Generally, the leaching rate from dispersed particulates is controlled by 1) diffusion and boundary layer effects around the limited surface area available to water; 2) the activation energy needed to disrupt the crystal and to thereby cause dissolution, and 3) the absolute solubility of the material. Solubility of copper is strongly dependent on the pH, and for the hydroxide is about 0.01 ppm at pH 10, 2 ppm at pH 7, but is 640 ppm at pH 4. Wood has a "pH" between 4 and 5. Therefore, copper hydroxides are a component of the preferred substantially crystalline (or amorphous sparingly soluble) copper material, as the hydroxides will raise the pH of the water in the wood. Additionally, alkali-metal bases, such as alkali-metal hydroxides, alkali-metal carbonates, and less preferred alkali-metal salts of organic carboxylic and/or sulfonic acid containing material having 1-4 carbon atoms per acid moiety, can be included in the liquid portion of the injected slurry to neutralize wood. Other useful bases include tribasic alkali phosphates and alkali borate salts.

Leaching will be discussed extensively infra Advantageously, the particulates of the present invention provide at 240 hours into an AWPA E11-97 leach test a total leached copper value that is within a factor of two above, to within a factor of five below, preferably within a factor of three below, the total leached copper value obtained by a wood sample treated with CCA and subjected to the same test.

By "substantially free of hazardous material" we mean the preservative treatment is substantially free of materials such as lead, arsenic, chromium, and the like. By substantially free of lead we mean less than 0.1% by weight, preferably less than 0.01% by weight, more preferably less than 0.001% by weight, based on the dry weight of the wood preservative. By substantially free of arsenic we mean less than 5% by weight, preferably less than 1% by weight, more preferably less than 0.1% by weight, for example less than 0.01% by weight, based on the dry weight of the wood preservative. By substantially free of chromium we mean less than 0.5% by weight, preferably less than 0.1% by weight, more preferably less than 0.01% by weight, based on the dry weight of the wood preservative.

By "environmentally responsible" we mean the wood preservative (including co-biocide) has a bioactive effectiveness that is at least about equal to that of injected copper-amine preservatives. Further, the environmentally responsible material is substantially free of small nanoparticles which can be readily flushed from wood. Therefore, in preferred embodiments of the invention the $d_5$ is greater than 5 nanometers, preferably greater than about 20 nanometers. Nanoparticle-sized metal particulates may be toxic to certain aquatic life, though the data is very preliminary. Additionally, environmentally responsible wood preservatives are beneficially substantially free of organic solvents. By substantially free we mean the treatment comprises less than 10% organic solvents, preferably less than 5% organic solvents, more preferably less than 1% organic solvents, for example free of organic solvents, based on the weight of the sparingly soluble and substantially insoluble biocides in the wood preservative.

By "injectable" we mean the wood preservative particulates are able to be pressure-injected into wood, wood products, and the like to depths normally required in the industry, providing an effective dispersion of biocidal particles throughout the injected volume, using equipment, pressures, exposure times, and procedures that are the same or that are substantially similar to those currently used in industry. Pressure treatment is a process performed in a closed cylinder that is pressurized, forcing the chemicals into the wood. Copper loading, also called copper retention is a measure of the amount of preservative that remains in the wood after the pressure is released. It is given as "pcf," or pounds of preservative per cubic foot of wood. Retention levels that must be reached are dependent on three variables: the type of wood used, the type of preservative used, and the use of the wood after treatment. The sparingly soluble copper-salt particulates of this invention are typically expected to be added to wood in an amount equal to or less than 0.25 pounds as copper per cubic foot. In preferred embodiments of the invention incising is not expected to be required to inject the slurries of the present invention into lumber having thicknesses of 6 to 10 inches.

Injectability requires the particulates be substantially free of the size and morphology that will tend to accumulate and form a filter cake, generally on or near the surface of the wood, that results in undesirable accumulations on wood in one or more outer portions of the wood and a deficiency in an inner portion of the wood. Injectability is generally a function of the wood itself, as well as the particle size, particle morphology, particle concentration, and the particle size distribution.

Another key aspect of the invention is to make a variety of biocidal particulate slurries available that are injectable into wood, thereby serving as a particulate wood preservative. Requirements of injectability into wood for substantially round, e.g., the diameter is one direction is within a factor of two of the diameter measured in a different direction, such as would be found in milled particles, are:

1) the $d_{96}$ is equal to or less than about 1 micron, but is preferably about 0.7 microns or less, more preferably about 0.5 microns or less, for example equal to or less than about 0.3 microns, or equal to or less than about 0.2 microns;

2) the $d_{99}$ is equal to or less than about 2 microns, preferably equal to or less than 1.5 microns, more preferably equal to or less than about 1 micron; and 3), the $d_{50}$ is less than 0.5 microns, preferably less than 0.4 microns, and the $d_{50}$ is greater than 0.02 microns, more preferably greater than 0.05 microns, for example a slurry where the $d_{50}$ is between about 0.1 microns and about 0.3 microns. We believe the first criteria primarily addresses the phenomena of bridging and subsequent plugging of pore throats, the second criteria addresses the phenomena of forming a filter cake, and the third criteria addresses the issue of having particulates disposed in the wood which have an optimum size to ensure the treatment has an acceptable bio-activity and lifetime. Once a pore throat is partially plugged, complete plugging and undesired buildup generally quickly ensues.

However, there are minimum preferred particulate diameters for the wood treatment, which depend somewhat on the copper salt(s) that are in the particulates. If the salts have a high solubility, very small particulates having a large surface to mass ratio will result in too high a copper ion concentration, and too fast a copper leaching, compared to preferred embodiments of this invention. Generally, it is preferred that for sparingly soluble copper or zinc salts, the $d_{20}$ be above 0.01 microns in diameter, preferably greater than 0.03 microns, for example greater than 0.06 microns in diameter. While organic biocide particles can be smaller than the sparingly soluble copper salt particles, as these compounds generally exhibit lower solubility in water than do the sparingly soluble copper salts, nevertheless a preferred minimum $d_{20}$ for organic biocide particulates is also 0.01 microns.

By injectable, unless otherwise specified we mean injectable into normal southern pine lumber. This invention also encompasses injecting the particulates into other woods as well as into for example heartwood. Selected other woods and heartwood may require a smaller substantially lower criteria on particle dimensions for injectability, and such formulations can be made as discussed herein, but the formulation most of interest is a commercially operative formulation developed for normal Southern Pine. Such a formulation will typically be useful for all other woods.

By "non-staining/non-coloring" we mean the wood preservative does not impart undesired color to the wood. Large particulates, or large agglomerations of smaller particulates, impose a visible and undesired color to the treated wood, which for copper is generally bluish or greenish. Surprisingly, visible coloring is usually indicative of poor injectability or agglomeration. Individual particles of diameter less than about 0.5 microns that are widely dispersed in a wood matrix do not color a wood product to any substantial degree. Filter cake forms unsightly coloring. An aggregation of particles, similar to filter-cake, could contribute un-wanted color. Preferably the $d_{99.5}$ is less than 1 micron. Even particulates having a size greater than 0.5 microns can impart very visible color, and agglomerates of similar size have the same effect as do large particles. In a preferred embodiment of the invention, the $d_{95}$ and more preferably the $d_{98}$ of the particulates and aggregates of particulates in the wood are smaller than 0.5 microns, for example equal to or less than 0.35 microns, more preferably equal to or less than than 0.3 microns. Certain compounds, particularly basic copper carbonate, copper hydroxide, basic copper phosphate, and copper oxychloride are preferred because they impart less color than do other particles of comparable size.

Additionally, the presence of a zinc salt, a magnesium salt, or both either as a separate phase or as a mixed phase may also reduce color. In one embodiment, fine particulates of iron oxide can be included in the injectable slurry to help mask any visible color, and also to act as a UV blocker to protect the surface of the wood. The finely ground iron oxides are comparable to or smaller than the injectable particulates comprising the sparingly soluble copper or zinc salts, or the particles comprising solid substantially insoluble organic biocide material.

By "inexpensive" we mean the wood preservative is prepared using techniques so that the cost of the wood treatment is competitive with for example copper-ethanolamine-complex treatments and other commonly used treatments. As the cost of copper is substantially constant regardless of the source, inexpensive relates primarily to the costs of manufacture, separation, sizing, and preservation of the particulate material. There are many techniques to create very small nanoparticles, but most of these processes are far too costly to be useful in the mass production of a copper-based wood preservative treatment. Generally, the term "inexpensive" means at a processed cost less than or equal to the current costs of the soluble copper-co-biocide treatments.

The preferred method of production of the sparingly soluble copper and zinc salts begins with a precipitation process, in the absence of water/solvent emulsions and the like. Preferably the reactants are of standard industrial quality, as opposed to higher levels of purity. Feedstock of sparingly soluble salts, organic biocides, and the like can be obtained commercially. The particles start with certain characteristics including size distribution and morphology, e.g., having a $d_{50}$ of between 1 to 8 microns. Surprisingly, the d50 of the feedstock is relatively unimportant. The critical step in the cost-effective manufacturing of injectable sparingly soluble copper salt particles, injectable sparingly soluble copper oxide particles, injectable sparingly soluble zinc salt particles, injectable sparingly soluble zinc oxide particles, and injectable sparingly soluble or substantially insoluble organic biocide particles, is wet milling. Particles made by other processes, particularly emulsion precipitation processes and fuming processes, are not sufficiently cost effective to manufacture commercially acceptable copper particulates for wood preservation.

Generally, the presence of any salt will induce corrosion. The wood preservatives of the present invention have a reduced tendency, compared to a similar concentration of copper obtained from the soluble copper treatments such as the amine-copper-complex treatments and alkanolamine-copper-complex treatments in use today, to corrode of metal that contacts the wood. The degree of corrosion will depend in large part on the salts selected, as well as on adjuvants including the dispersants and stabilizers.

We also believe that another problem with the soluble amine-complexed copper preservatives is that the commonly used soluble copper compounds provide nitrogen-containing nutrients (amines) which are believed to act as food-stuff and causes an increase in the presence of sapstain molds, therefore requiring additional biocides effective on sapstain molds to be added to protect the appearance of the wood. When there is also bio-available carbon sources, in addition to bio-available nitrogen, the problem is made worse. Advantageously, the wood preservative is substantially free of any amines other than certain selected amines that may be used as a supplemental biocide. By substantially free we mean the treatment comprises less than 20% amines, preferably less than 10% amines, for example less than 5% amines, more preferably less than 1% amines, alternately free of amines, based on the weight of the sparingly soluble or substantially insoluble biocides in the wood preservative. Alternatively, the term means there is less than one amine molecule or moiety per four copper atoms, preferably less than one amine molecule or moiety per ten copper atoms. Again, amines that are used as supplemental biocides, if any, are excluded from this limitation. While basic copper nitrate is a useful sparingly soluble copper salt for use in this invention, in most embodiments of the invention the wood preservative is also substantially free of nitrates.

Another embodiments of the invention is an injectable particulate preservative for wood that is substantially free of bio-available nitrogen, and also is substantially free of bio-available carbon. By substantially free of bio-available nitrogen we mean the treatment comprises less than 10% of nitrates and organic nitrogen, preferably less than 5% of nitrates and organic nitrogen, more preferably less than 1% of nitrates and organic nitrogen, for example less than 0.1% of nitrates and organic nitrogen, based on the weight of the copper in the wood preservative. In most of the soluble or complexed copper treatments, there are between 1 and 4 atoms of organic nitrogen that act as a complexer or carrier for one atom of copper. In the preferred embodiments of this invention, there is less than 0.3 atoms, preferably less than 0.1 atoms, for example less than 0.05 atoms of organic nitrogen per atom of copper in the wood preservative treatment. Again, organic nitrogen-containing compounds that are used specifically as supplemental biocides are excluded from this limitation. By substantially free of bio-available carbon we mean the treatment comprises less than 40% of bio-available organic material (defined as material that is degradable or that will during the lifespan of the treatment will become degradable), preferably less than 20% of bio-available organic material, more preferably less than 10% of bio-available organic material, based on the weight of the copper in the wood preservative. Again, organic compounds that are used as supplemental biocides, if any, are excluded from this limitation. It is believed that the presence of bio-available organic carbon may encourage the growth of certain molds.

In one embodiment, the copper-based particles are substantially free of polymers, such as organic polymers. By substantially free, it is meant that the biocide-containing particles are less than about 50% by weight polymer, preferably less than about 35% by weight polymer, for example, less than 25% by weight polymer, such as less than 15% by weight polymer. In one embodiment, the copper-based particles are essentially free of polymer, by which it is meant the copper-based particles comprise less than about 5% by weight polymer. Generally, polymers, if present, should be limited to the lowest practicable amount necessary to act as functional dispersants/stabilizers. The ratio of the weight of copper present in the particles to polymer present in the particles may be at least about 1 to 1, for example at least about 2 to 1, 4 to 1, 5 to 1, 7 to 1, or at least about 10 to 1. For example, if ratio of the weight of copper present in the particles to the weight of polymer present in the particles is at least about 2 to 1, the particles comprise at least about twice as much copper by weight as polymer.

By "substantially crystalline" we mean for example greater than about 30%, preferably greater than about 50%, by weight of the material of interest (copper salt, zinc salt, and the like) is crystalline. A material is substantially crystalline if the material give the distinctive X-ray diffraction patterns of the crystalline entity (relating to d spacing, not present in the amorphous material). The preferred method for determining crystallinity is by calorimetry, by measuring the heat of dissolution of the sample in a solvent and comparing this heat with the measured heats of amorphous and crystalline standard of the same salt, provided the dissolution of the crystalline salt is substantially different than the dissolution of the corresponding amorphous salt.

As crystallinity is difficult to measure, the following exemplary compounds meet the requirements for substantially crystalline copper compounds: copper(II) borate; copper boride ($Cu_3B_2$); yellow copper(I) carbonate; basic copper carbonate; copper(II) carbonate dihydroxide ($CuCO_3 \times Cu(OH)_2$); copper(II) carbonate dihydroxide ($2CuCO_3 \times Cu(OH)_2$); copper (I and II) chloride; copper(II) chloride$\times 2H_2O$; copper oxychloride ($CuCl_2 \times Cu(OH)_2$); copper(I and II) cyanide; copper(I and II) fluoride; copper(II) formate; copper(I and II) oxide; copper phosphate$\times 3$ water; copper(I and II) sulfate; basic copper phosphate, basic copper phosphosulfate, tribasic copper sulfate; copper silicate, and copper(I) thiocyanate. The term (I and II) means the copper(I) salt and the copper(II) salt. These salts are further considered substantially crystalline with as much as 10% by weight based on the weight of the copper being substituted with magnesium, zinc, or both. The following exemplary compounds meet the requirements for substantially crystalline zinc compounds: zinc carbonate; zinc chloride; zinc cyanide; zinc diphosphate; zinc fluoride; zinc fluoride$\times 4$ water; zinc hydroxide; zinc oxide; zinc phosphate; and zinc sulfate. These salts are further defined as substantially crystalline with as much as 10% by weight based on the weight of the zinc being substituted with magnesium, copper, or both. The following exemplary compounds meet the requirements for substantially crystalline tin compounds: tin(II) diphosphate (pyrophosphate); tin(II) phosphate ($Sn_3(PO_4)_2$); and tin(II) sulfate.

Several of the copper salts described herein are available in crystalline and in amorphous phases. Generally crystallinity is preferred, as the lattice energy of the crystal is expected to slow down dissolution. However, amorphous copper salts are useful in the invention, and for the less soluble salts the amorphous phases may be preferred over crystalline phases. Phosphate-stabilized copper hydroxide, a preferred sparingly soluble copper hydroxide used in embodiments of this invention, is typically substantially amorphous. Amorphous sparingly soluble salts are equally effective, and they can be treated with one or more coatings, or can be made of a particular size, or of more insoluble salts, such that the amorphous material may easily have release and leach characteristics like the substantially crystalline salts. And discussion relating to substantially crystalline should be considered a preferred variant of the invention, as the same disclosure is generally equally applicable to amorphous material, or substantially amorphous material.

As used herein, the term "copper-containing particulate" as it pertains to wood preservatives means a particle having a size between about 0.7 microns and about 0.01 microns that comprises at least one sparingly soluble copper salt. The term "particle" is used interchangeably with the term "particulate," while the term "nanoparticle" refers to particles having a size less than about 0.01 microns in diameter. The term "copper" includes, unless specifically stated otherwise, the cuprous ion, the cupric ion, or mixture thereof, or combination thereof. The term "copper-containing" means the particle comprises at least about 20%, 30%, 50%, or 75% by weight of one or more sparingly soluble copper compounds. In another embodiment, essentially all (e.g., more than 95%) of the weight of the copper-containing particles are composed of sparingly soluble copper compounds.

As used herein, the term "zinc-containing particulate" as it pertains to wood preservatives means a particle having a size between about 0.7 microns and about 0.01 microns that comprises at least about 20%, 30%, 50%, or 75% by weight of one or more substantially crystalline or sparingly soluble zinc compounds. In another embodiment, essentially all (e.g., more than 95%) of the weight of the zinc-containing particles is composed of one or more substantially crystalline or sparingly soluble zinc compounds. The preferred sparingly soluble zinc-containing materials are zinc hydroxide, zinc borate ($Zn(BO_2)_2 \times H_2O$), and zinc carbonate. Again, if the borate is used as the anion, preferably the composition also comprises one or more salts of carbonate or hydroxide to maintain a slightly elevated pH within the wood matrix, to slow dissolution of the borate salts. If zinc-based particulates are used, they are advantageously used with copper-based particulates.

As used herein, the term "tin-containing particulate" as it pertains to wood preservatives means a particle having a size between about 0.7 microns and about 0.01 microns that comprises at least one sparingly soluble tin salt. Generally, tin-based particulates are not preferred because tin does not have the desired bio-activity. Tin oxides are believed to be particularly inert. The preferred sparingly soluble tin material are tin hydroxides, $Sn(OH)_2$ and $Sn(OH)_4$.

Preferred particles comprise at least 30%, preferably at least 50%, more preferably at least 70%, for example between about 80% and about 98% by weight of total of copper hydroxides, copper(I) oxide, basic copper carbonates, copper carbonates, copper oxychloride, basic copper phosphate, basic copper phosphosulfate, tribasic copper sulfate, alkaline copper nitrate, basic copper borate, copper silicate, or mixtures thereof. The various particles within a wood preservative can comprise different biocides, even different sparingly soluble copper salts. For example, a treatment may contain particles that comprise copper borate or copper borate in combination with copper hydroxide and/or basic copper salt, particularly basic copper carbonate, other particles that comprise basic copper carbonate, optionally particles that comprise basic copper phosphate, and even other particles that comprise copper oxide. The particles having different phases may in preferred embodiments be of different sizes, depending on the copper material present.

In one embodiment, exemplary wood preservatives have a $d_{50}$ equal to or smaller than 0.5 μm, 0.25 μm, 0.2 μm, or 0.15 μm. Advantageously, the $d_{96}$, and preferably the $d_{99}$, are within a factor of three of the $d_{50}$, and very preferably is less than 1.2 microns. In one embodiment, the $d_{50}$ is at least 25 nanometers, for example, at least 50 nanometers.

There is a large number of references describing how to make copper-containing "nanoparticles." These references generally can not be used to manufacture the particulates at the desired cost. One method that is particularly not cost effective is using an emulsion precipitation or emulsion crystallization technique, where small particles are allowed to grow in a certain phase of an emulsion, where the ultimate size of the particle is limited by the amount of a component in a droplet in the emulsion. Both inorganic salts and organic biocidal particulates can be formed in this manner, but not at a cost where such materials would be useful for foliar applications on crops nor for wood preservation.

In one embodiment of the invention, a preliminary copper-based particles are prepared, such as by precipitation, from a mixture comprising copper and an amine. The copper and amine may be present in the form of a copper-amine complex. Preferred precipitates comprise copper hydroxides. The particles may be prepared by modifying a pH of the mixture comprising copper and the amine, surprisingly in a downward direction to pH 6 or with an alkali hydroxide to obtain a pH greater than about 13. A dispersant may be added to the mixture before obtaining the precipitate. In one embodiment, the pH is adjusted so that the pH is between about 5.5 to about 7. Suitable acids for adjusting the pH include, for example, sulfuric acid, nitric acid, hydrochloric acid, formic acid, boric acid, acetic acid, carbonic acid, sulfamic acid, phosphoric acid, phosphorous acid, and/or propionic acid. The anion of the acid used may be partially incorporated in the precipitated salt, as may other cations, such as magnesium and/or zinc.

Another embodiment of a method for preparing copper-based particles comprises precipitation of copper-based particles from a solution comprising (a) copper, such as in the form of a copper salt, and (b) a pH modifying agent, such as a hydroxide. Exemplary hydroxides may be selected from hydroxides of group 1a and/or group 2a elements, such as sodium and potassium hydroxide.

U.S. Pat. No. 4,808,406, the disclosure of which is incorporated by reference, describes a useful method for producing finely divided stable cupric hydroxide composition of low bulk density comprising contacting solutions of an alkali metal carbonate or bicarbonate and a copper salt, precipitating a basic copper carbonate-basic copper sulfate to a minimum pH in the range of greater than 5 to about 6, contacting the precipitate with an alkali metal hydroxide and converting basic copper sulfate to cupric hydroxide. Another method of manufacturing the copper compounds is the method described in U.S. Pat. No. 4,404,169, the disclosure of which is incorporated by reference. This patent describes a process of producing cupric hydroxides having stability in storage if phosphate ions are added to a suspension of copper oxychloride in an aqueous phase. The copper oxychloride is then reacted with alkali metal hydroxide or alkaline earth metal hydroxide, and the cupric hydroxide precipitated as a result of the suspension is washed and then re-suspended and subsequently stabilized by the addition of acid phosphate to adjust a pH value of 7.5 to 9. The suspended copper oxychloride is preferably reacted in the presence of phosphate ions in an amount of 1 to 4 grams per liter of the suspension and at a temperature of 20° to 25° C. and the resulting cupric hydroxide is stabilized with phosphate ions.

There are numerous methods of preparing very small particles of copper salts, and the above list is exemplary and not complete. It is important to note that the size of the precipitates is relatively unimportant, and the cost of the reagents is exceedingly important. The material need not be of high purity. Indeed, it is desirable to have one or more "contaminants" in the precipitating solutions. Smaller diameters are obtained when the concentration of impurities such as Mg, Ca, Zn, Na, Al and Fe in the suspension is high. Fe present in the suspension acts especially strongly to prevent formation of large-diameter cuprous hydroxide particles.

Copper hydroxide is not particularly stable. Hydroxides can be changed to oxides for example in a quick and exothermic reaction by exposure of the copper hydroxide particles to aqueous solution of glucose. Copper hydroxide may react with air, sugars, or other compounds to partially or completely form copper oxide. The conditions for conversion are highly favored during kiln-drying treated wood, which contains gluconuuronic acids, which are sugar-like molecules, and heat and a dehydrating condition. However, as taught by U.S. Pat. No. 3,231,464, the disclosure of which is incorporated herein by reference thereto, the presence of magnesium or magnesium and zinc can help stabilize cupric hydroxide from converting to copper oxide via the loss of a water molecule. The preferred copper hydroxide particles used in this invention are stabilized. U.S. Pat. No. 3,231,464 teaches stabilizing the copper hydroxide with added magnesium zinc, or both, at a Cu:Mg and/or Cu:Zn weight ratio of 8:1. Copper hydroxide prepared in a manner so as to contain significant magnesium and/or zinc hydroxides are more stable and resistant to degradation to copper oxides. The preferred copper hydroxide particles comprise between 50% and 90 copper hydroxide, with the remainder comprising zinc hydroxide, magnesium hydroxide, or both.

In one embodiment of the invention, copper-based particles are precipitated from a mixture of a copper salt solution and a hydroxide (and optionally other anions) in the presence of at least one group 2a metal or salt thereof, such as magnesium or a magnesium salt. In one embodiment, the copper-based particles are precipitated from a mixture comprising at least about 0.05 parts magnesium, for example at least about 0.1 parts magnesium per 9 parts copper. The mixture may comprise at least about 0.25 parts magnesium per 9 parts copper. The mixture may comprise less than about 1.5 parts magnesium, for example, less than about 1.0 parts, or less than about 0.75 parts magnesium per 9 parts copper. Copper-based particles prepared in accordance with the present invention will comprise a group 2a metal or zinc if such materials (metal ions) were used in preparation of the particles. In another embodiment, the copper-based particles are precipitated from a mixture comprising at least about 0.2 parts magnesium, for example at least about 0.25 parts magnesium per 22.5 parts copper. The mixture may comprise at least about 0.5 parts magnesium per 22.5 parts copper. The mixture may comprise less than about 3.5 parts magnesium, for example, less than about 2.5 parts magnesium, or less than about 2 parts magnesium per 22.5 parts copper. The parts here merely reflect weight ratios of the cations in the solution to be precipitated, and the parts do not imply concentration.

Alternatively, or in combination with the group 2a metal or salt thereof, the copper-based particles may be precipitated from a solution comprising zinc metal or salt thereof. For example, the mixture may comprise at least about 0.1 parts zinc, for example, at least about 0.25 parts zinc, at least about 1.0 parts zinc, or at least about 2.0 parts zinc per 22.5 parts copper. The mixture may comprise less than about 3.0 parts zinc, for example, less than about 2.5 parts zinc, or less than about 1.5 parts zinc per 22.5 parts copper. Preferably, the mixture additionally comprises at least about 0.25 parts magnesium, for example, at least about 0.5 parts magnesium, at least about 1.0 parts magnesium, or at least about 2 parts magnesium per 22.5 parts copper. The mixture may comprise less than about 5.0 parts magnesium, for example, less than about 2.5 parts magnesium, or less than about 2 parts magnesium per 22.5 parts copper.

While various precipitation methods can provide small particles of sparingly soluble salts, the product usually has a small fraction of particles that are unacceptably large. A very small fraction of particles having a particle size above about 1 micron causes, in injection tests on wood specimens, severely impaired injectability. Large particles, e.g., greater than about 1 micron in diameter, should be broken down by wet-milling. Even for processes that provide very small median diameter particles, say a few tenths of a micron in diameter, the precipitation process seems to result in a small fraction of particles that are larger than about 1 micron, and these particles plug up pores and prevent acceptable injectability. The $d_{99}$, preferably the $d_{99.5}$, of injectable particles is less than about 1 micron. Additionally, wet milling preferentially breaks down rod-shaped particles, which are particularly troublesome.

We have surprisingly found that wet ball milling, with milling media of specified characteristics, can advantageously modify particle size and morphology of sparingly soluble copper salts, sparingly soluble zinc salts, copper oxides, zinc oxides, iron oxides, and even solid organic biocides known to be highly resistant to milling, such as chlorothalonil, to a size where the compounds are readily injectable into wood. This finding is central to the invention. We have surprisingly found that both organic and inorganic particulates can be readily milled into an injectable material by wet milling with a milling material such as a 0.3 to a 0.7 mm milling media having density greater than 3 grams/cm$^3$, for example equal to or greater than 3.8 grams/cm$^3$ such as 0.5 mm diameter zirconium silicate, preferably greater than 5.5, grams/cm$^3$ provided by a 0.5 mm milling bead of zirconium oxide which may contain one or more dopants such as cerium and/or yttrium, and/or magnesia in a stabilizing amount. Additionally, regardless of the particle size of the feedstock, the particles can be broken down to injectable size in a matter of minutes to at most a few hours. Beneficially all injectable formulations for wood treatment should be wet-milled, even when the "mean particle size" is well within the range considered to be "injectable" into wood.

The milling media, also called grinding media or milling beads, is central to this invention. The selection of milling media is expressly not a routine optimization. The use of this media allows an average particle size and a narrow particle size distribution that had previously not been obtainable in the art, nor did the results in the prior art allow one to predict the unexpected results we obtained. A major contribution of this invention is a method of preparing a particulate biocide product having a $d_{50}$ equal to or less than about 1 micron, comprising the steps of: 1) providing the solid inorganic or organic biocide, and a liquid comprising a surface active agent, to a mill; providing a milling media comprising an effective amount of milling beads having a diameter between 0.1 mm and 0.8 mm, preferably between about 0.2 mm and about 0.7 mm, more preferably between about 0.3 mm and about 0.6 mm, wherein these milling beads have a density greater than about 3 grams/cm3, preferably equal to or greater than 3.5 grams/cm3, more preferably equal to or greater than 3.8 grams/cm3, most preferably equal to or greater than 5.5 grams/cm3, for example a zirconia bead having a density of about 6 grams/cm3; and 2) wet milling the material at high speed, for example between 300 and 6000 rpm, more preferably between 1000 and 4000 rpm, for example between about 2000 and 3600 rpm, where milling speed is provided for a laboratory scale ball mill, for a time sufficient to obtain a product having a mean volume particle diameter of about 1 micron or smaller, for example between about 5 minutes and 300 minutes, preferably from about 10 minutes to about 240 minutes, and most preferably from about 15 minutes to about 60 minutes. As little as 5% by volume of the milling media need be within the preferred specifications for milling some materials, but better results are obtained if greater than 10% by weight, preferably greater than 25% by weight, for example between 40% and 100% by weight of the milling material is within the preferred specifications. For milling material outside the preferred specifications, advantageously this material has a density greater than 3 grams/cm$^3$ and a diameter less than 4 mm, for example 1 or 2 mm zirconia or zirconium silicate milling beads.

The milling media advantageously comprises or consists essentially of a zirconium-based material. The preferred media is zirconia (density ~6 g/cm$^3$), which includes preferred variants such as yttria stabilized tetragonal zirconium oxide, magnesia stabilized zirconium oxide, and cerium doped zirconium oxide. For some biocides, zirconium silicate (density ~3.8 g/cm$^3$) is useful. However, for several biocides such as chlorothalonil, zirconium silicate will not achieve the required action needed to obtain the narrow sub-micron range of particle sizes in several preferred embodiments of this invention. In an alternate embodiment, at least a portion of the milling media comprises or consists essentially of metallic material, e.g., steel. The milling medium is a material having a density greater than about 3.5, preferably at least about 3.8, more preferably greater than about 5.5, for example at least about 6 g/cm$^3$.

We believe that density and particle size are the two most important parameters in the milling media. Preferably the milling media comprises or consists essentially of particles, having a size (diameter) between about 0.1 mm and about 0.8 mm, preferably between about 0.3 mm and about 0.7 mm, for example between about 0.4 mm and 0.6 mm. Also preferably, the milling media can have a density greater than about 3.8 g/cm$^3$, preferably greater than about 5.5 g/cm$^3$, more preferably greater than about 6 g/cm$^3$. The zirconium-based milling media useful in the present invention can comprise or consist essentially of particles having a diameter (as the term is used in the art) between about 0.1 mm and about 0.8 mm, preferably between about 0.3 mm and about 0.7 mm, for example between about 0.4 mm and 0.6 mm.

Not all the milling media need be the preferred material, e.g., having a preferred diameter between 0.1 mm and 0.8 mm, preferably between 0.2 mm and 0.7 mm, more preferably between 0.3 mm and 0.6 mm, and having a preferred density equal to or greater than 3.8 grams/cm$^3$, preferably greater than or equal to 5.5 grams/cm$^3$, more preferably greater than or equal to 6 grams/cm$^3$. In fact, as little as 10% of this media will provide the effective grinding. The amount of the preferred milling media, based on the total weight of media in the mill, can be between 5% and 100%, is advantageously between 10% and 100%, and is preferably between 25% and 90%, for example between about 40% and 80%. Media not within the preferred category can be somewhat larger, say 1 mm to 4 mm in diameter, preferably from 1 mm to 2 mm in diameter, and advantageously also has a density equal to or greater than 3.8 grams/cm$^3$.

A first aspect of the invention is a method of preparing a submicron biocide product comprising the steps of: 1) providing the solid biocide in particle form to a ball mill, providing a liquid to a mill, and providing a milling media to the mill, wherein the milling media comprises at least 5%, preferably at least 10%, more preferably at least 25% by weight of the milling media having a particle diameter between 0.1 to 0.8 mm, preferably between 0.3 and 0.7 mm, and having a density equal to or greater than 3.8 g/cm$^3$, preferably equal to or greater than 5.5 g/cm$^3$; and 2) milling the material for a time sufficient to obtain a product having a mean volume particle diameter $d_{50}$ of about 1 micron or smaller. The mill speed is advantageously fast, for example from 1000 rpm to about 4000 rpm, and the milling time is preferably between 10 minutes and 240 minutes.

Generally, less dense milling media will provide a relatively larger $d_{50}$, which can be useful for foliar applications.

The denser milling media, for example media having a density greater than 5.5 g/cm$^3$, provides a smaller $d_{50}$. Surprisingly, varying the milling time has very little effect on the $d_{50}$. The preferred dense milling media is zirconia, cerium doped zirconia. The zirconium oxide can comprise any stabilizers and/or dopants known in the art, including, for example, cerium, yttrium, and magnesium. An alternate useful dense milling material is steel. Generally, at least 25% by weight of the milling media must have a density greater than 3.8 and a diameter between 0.1 and 0.7 mm to reliably obtain injectable particles of sparingly soluble copper salts.

Manufacturing injectable solid substantially insoluble organic biocide particles, e.g., chlorothalonil, can beneficially be performed by 1) providing the chlorothalonil and a liquid comprising surface active agents to a mill, and 2) milling the material with a milling media having a density greater than 5.5 grams/$cm^3$, for example milling beads comprising a zirconium oxide having a diameter between about 0.1 mm and about 0.7 mm. The invention also encompasses a organic biocide particulate product, e.g., a chlorothalonil product, having a $d_{50}$ below about 1 micron, typically below about 0.5 microns, and preferably between 0.1 and 0.3 microns, which advantageously also exhibits a $d_{50}$ that is less than about three times the $d_{50}$, preferably less than about two times the $d_{50}$.

The attainment of the injectable size, which generally requires both a $d_{50}$ below 0.5 microns and a $d_{98}$ less than three times the $d_{50}$, was a surprising development. Milling sparingly soluble copper salts for several days with a 2 mm milling media could not provide the required particle size distribution, even if the feed material had a d50 of less than 0.3 microns. Milling a milling-resistant organic biocide with 1 mm zirconia provided a chlorothalonil product with a $d_{50}$ of 2 to 3 microns. Yet, surprisingly, milling each of these with a preferred milling media, e.g., zirconia-based milling beads having a diameter between 0.4 and 0.5 mm, provided each of these products in injectable sub-micron slurries in under a few hours, often in less than 30 minutes.

Advantageously, the liquid comprises one or more dispersants and/or stabilizers. The presence of these promotes a smaller d50 and a narrower particle size distribution, because agglomeration of particulates is discouraged. Aqueous dispersing agents for such dispersed solids are well known to those skilled in the art and include, but are not limited to, nonionic surfactants such as ethylene oxide/propylene oxide block copolymers, polyvinyl alcohol/polyvinyl acetate copolymers, polymeric nonionic surfactants such as the acrylic graft copolymers; anionic surfactants such as polyacrylates, lignosulfonates, polystyrene sulfonates, maleic anhydride-methyl vinyl ether copolymers, naphthalene sulfonic acid formaldehyde condensates, phosphate ester surfactants such as a tristyrenated phenol ethoxylate phosphate ester, maleic anhydride-diisobutylene copolymers, anionically modified polyvinyl alcohol/polyvinylacetate copolymers, and ether sulfate surfactants derived from the corresponding alkoxylated nonionic surfactants; cationic surfactants; zwitterionic surfactants; and the like.

The milling of the organic biocides is advantageously performed in the presence of an aqueous medium containing surfactants and/or dispersants, such as those known in the art. Use of other media, including for example polar organic solvents such as alcohols, generally does not offer added advantage sufficient to outweigh the cost and associated hazards of milling with solvents. Because it is now possible to achieve a smaller particle size and a narrower particle size distribution using the present invention than was previously known in the art, the number and amount of stabilizers and/or dispersants are less critical. As used herein, the term "surface active agent" includes both singular and plural forms and encompasses generally both stabilizers and dispersants. The surface active agent may be anionic, cationic, zwitterionic, or nonionic, or a combination thereof. Generally, higher concentrations of surface active agents present during milling result in a smaller particle size.

However, because we have surprisingly found a milling media and conditions where very small particles and a narrow particle size distribution are obtainable, we can use less/lower amounts of stabilizers and/or dispersants than would otherwise be used. For example, advantageously the total weight of surface active agents in the present invention can be less than about 1.5 times the weight of the particulate organic biocide, preferably less than about the weight of the particulate organic biocide. A stabilizing amount of the surface active agent can be used, generally not less than about 2%, and typically not more than about 60% by weight, based on the weight of the particulate organic biocide. Other adjuvants, such as: fillers including biocidal fillers such as zinc oxide and non-biocidal fillers such as silica; stabilizer/dispersants such as a poly(oxypropylene) block copolymer with poly(oxyethylene), commercially available from BASF, PROXEL GXL (1,2-benzisothiazolin-3-one, commercially available from ICI, and/or PVP K-30 poly(vinyl pyrrolidone), commercially available from BAS; typical viscosity modifiers/stabilizers such as xanthan gum commercially available from Kelco); typical antifoaming agents such as Antifoam FG-10, a silicon emulsion commercially available from Dow Corning; antifreeze such as propylene glycol; chelators such as EDTA, HEDP, and the like, can be added to the water before or during milling. Milling is best done in a wet mill or high speed media mill.

Examples of suitable classes of surface active agents include, but are not limited to, anionics such as alkali metal fatty acid salts, including alkali metal oleates and stearates; alkali metal lauryl sulfates; alkali metal salts of diisooctyl sulfosuccinate; alkyl aryl sulfates or sulfonates, lignosulfonates, alkali metal alkylbenzene sulfonates such as dodecylbenzene sulfonate, alkali metal soaps, oil-soluble (e.g., calcium, ammonium, etc.) salts of alkyl aryl sulfonic acids, oil soluble salts of sulfated polyglycol ethers, salts of the ethers of sulfosuccinic acid, and half esters thereof with nonionic surfactants and appropriate salts of phosphated polyglycol ethers; cationics such as long chain alkyl quaternary ammonium surfactants including cetyl trimethyl ammonium bromide, as well as fatty amines; nonionics such as ethoxylated derivatives of fatty alcohols, alkyl phenols, polyalkylene glycol ethers and condensation products of alkyl phenols, amines, fatty acids, fatty esters, mono-, di-, or triglycerides, various block copolymeric surfactants derived from alkylene oxides such as ethylene oxide/propylene oxide (e.g., PLURONIC™, which is a class of nonionic PEO-PPO co-polymer surfactant commercially available from BASF), aliphatic amines or fatty acids with ethylene oxides and/or propylene oxides such as the ethoxylated alkyl phenols or ethoxylated aryl or polyaryl phenols, carboxylic esters solubilized with a polyol or polyvinyl alcohol/polyvinyl acetate copolymers, polyvinyl alcohol, polyvinyl pyrrolidinones (including those sold under the tradenames AGRIMER™ and GANEX™), cellulose derivatives such as hydroxymethyl cellulose (including those commercially available from Dow Chemical Company as METHOCEL™), and acrylic acid graft copolymers; zwitterionics; and the like; and mixtures, reaction products, and/or copolymers thereof.

Additionally or alternatively, the surface active agent may include, but is not limited to, low molecular weight sodium lauryl sulfates, calcium dodecyl benzene sulfonates, tristyryl ethoxylated phosphoric acid or salts, methyl vinyl ether-maleic acid half-ester (at least partially neutralized), beeswax, water soluble polyacrylates with at least 10% acrylic acids/salts, or the like, or a combination thereof.

Additionally or alternatively, the surface active agent may include, but is not limited to, alkyl grafted PVP copolymers commercially available as GANEX™ and/or the AGRIMER™ AL or WP series, PVP-vinyl acetate copolymers commercially available as the AGRIMER™ VA series, lignin sulfonate commercially available as REAX 85A (e.g., with a molecular weight of about 10,000), tristyryl phenyl ethoxylated phosphoric acid/salt commercially available as SOPROPHOR™ 3 D33, GEROPON™ SS 075, calcium dodecylbenzene sulfonate commercially available as NINATE™ 401 A, IGEPAL™ CO 630, other oligomeric/polymeric sulfonated surfactants such as Polyfon H (molecular weight ~4300, sulfonation index ~0.7, salt content ~4%), Polyfon T (molecular weight ~2900, sulfonation index ~2.0, salt content ~8.6%), Polyfon O (molecular weight ~2400, sulfonation index ~1.2, salt content ~5%), Polyfon F (molecular weight ~2900, sulfonation index ~0.3.3, salt content ~12.7%), Reax 88B (molecular weight ~3100, sulfonation index ~2.9, salt content ~8.6%), Reax 100 M (molecular weight ~2000, sulfonation index ~3.4, salt content ~6.5%), and Reax 825 E (molecular weight ~3700, sulfonation index ~3.4, salt content ~5.4%), and the like.

Other notable surface active agents can include nonionic polyalkylene glycol alkyd compounds prepared by reaction of polyalkylene glycols and/or polyols with (poly)carboxylic acids or anhydrides; A-B-A block-type surfactants such as those produced from the esterification of poly(12-hydroxystearic acid) with polyalkylene glycols; high molecular weight esters of natural vegetable oils such as the alkyl esters of oleic acid and polyesters of polyfunctional alcohols; a high molecular weight (MW>2000) salt of a naphthalene sulfonic acid formaldehyde condensate, such as GALORYL™ DT 120L available from Nufarm; MORWET EFW™ available from Akzo Nobel; various Agrimer™ dispersants available from International Specialties Inc.; and a nonionic PEO-PPO-PEO triblock co-polymer surfactant commercially available as PLURONIC™ from BASF.

Other examples of commercially available surface active agents include Atlox 4991 and 4913 surfactants (Uniqema), Morwet D425 surfactant (Witco), Pluronic P105 surfactant (BASF), Iconol TDA-6 surfactant (BASF), Kraftsperse 25M surfactant (Westvaco), Nipol 2782 surfactant (Stepan), Soprophor FL surfactant (Rhone-Poulenc), Empicol LX 28 surfactant (Albright & Wilson), Pluronic F108 (BASF).

In one embodiment, exemplary suitable stabilizing components include polymers or oligomers having a molecular weight from about 250 to about $10^6$, preferably from about 400 to about $10^5$, more preferably from about 400 to about $10^4$, and can include, for example, homopolymers or co-polymers described in "Polymer Handbook," 3rd Edition, edited by J. Brandrup and E. H. Immergut.

In another embodiment, exemplary suitable stabilizing components include polyolefins such as polyallene, polybutadiene, polyisoprene, poly(substituted butadienes) such as poly(2-t-butyl-1,3-butadiene), poly(2-chlorobutadiene), poly(2-chloromethyl butadiene), polyphenylacetylene, polyethylene, chlorinated polyethylene, polypropylene, polybutene, polyisobutene, polybutylene oxides, copolymers of polybutylene oxides with propylene oxide or ethylene oxide, polycyclopentylethylene, polycyclohexyiethylene, polyacrylates including polyalkylacrylates and polyarylacrylates, polymethacrylates including polyalkylmethacrylates and polyarylmethacrylates, polydisubstituted esters such as poly(di-n-butylitaconate), poly(amylfumarate), polyvinylethers such as poly(butoxyethylene) and poly(benzyloxyethylene), poly (methyl isopropenyl ketone), polyvinyl chloride, polyvinyl acetate, polyvinyl carboxylate esters such as polyvinyl propionate, polyvinyl butyrate, polyvinyl caprylate, polyvinyl laurate, polyvinyl stearate, polyvinyl benzoate, polystyrene, poly-t-butyl styrene, poly (substituted styrene), poly(biphenyl ethylene), poly(1,3-cyclohexadiene), polycyclopentadiene, polyoxypropylene, polyoxytetramethylene, polycarbonates such as poly(oxycarbonyloxyhexamethylene), polysiloxanes, in particular, polydimethyl cyclosiloxanes and organo-soluble substituted polydimethyl siloxanes such as alkyl, alkoxy, or ester substituted polydimethylsiloxanes, liquid polysulfides, natural rubber and hydrochlorinated rubber, ethyl-, butyl- and benzyl-celluloses, cellulose esters such as cellulose tributyrate, cellulose tricaprylate, and cellulose tristearate, natural resins such as colophony, copal, and shellac, and the like, and combinations or copolymers thereof.

In still another embodiment, exemplary suitable stabilizing components include co-polymers of styrene, alkyl styrenes, isoprene, butenes, butadiene, acrylonitrile, alkyl acrylates, alkyl methacrylates, vinyl chloride, vinylidene chloride, vinyl esters of lower carboxylic acids, and $\alpha,\beta$-ethylenically unsaturated carboxylic acids and esters thereof, including co-polymers containing three or more different monomer species therein, as well as combinations and copolymers thereof.

In yet another embodiment, exemplary suitable stabilizing components include polystyrenes, polybutenes, for example polyisobutenes, polybutadienes, polypropylene glycol, methyl oleate, polyalkyl(meth)acrylate e.g. polyisobutylacrylate or polyoctadecylmethacrylate, polyvinylesters e.g. polyvinylstearate, polystyrene/ethyl hexylacrylate copolymer, and polyvinylchloride, polydimethyl cyclosiloxanes, organic soluble substituted polydimethyl siloxanes such as alkyl, alkoxy or ester substituted polydimethylsiloxanes, and polybutylene oxides or copolymers of polybutylene oxides with propylene and/or ethylene oxide. In one embodiment, the surface active agent can be adsorbed onto the surface of the biocide particle, e.g., in accordance with U.S. Pat. No. 5,145,684.

Another aspect of the invention is a method of preparing a submicron organic biocide product for use as a foliar treatment, or as an additive in paints or coatings, comprising the steps of: 1) providing the organic biocide to a mill, and 2) milling the material with a milling media having a density greater than about 3.5 and having a diameter between about 0.1 mm and about 0.7 mm. The density of the milling media, and especially of the milling media within the size range 0.3 to 0.7 mm, is advantageously greater than about 3.8, for example greater than about 4, preferably greater than about 5.5, for example equal to or greater than about 6 grams per cubic centimeter. Ceramic milling media is preferred over metallic milling media.

In each embodiment, the milling load is preferably about 50% of the volume of the mill, though loadings between 40% and 80% are efficient. In each embodiment, advantageously water and surface active agents are added to the product before or during milling. In each embodiment, the product can be transported as a stable slurry, as a wettable powder, or as granules that disintegrate on mixing with water to release the product.

Wet milling can be done in a sand grinder charged with for example partially stabilized zirconia beads with diameter 0.5 mm; alternately wet milling in a rotary sand grinder with partially stabilized zirconia beads with diameter 0.5 mm and with stirring at for example 1000 rpm; or by use of a wet-ball mill, an attritor (e.g., manufactured by Mitsui Mining Ltd.), a perl mill (e.g., manufactured by Ashizawa Ltd.), or the like. Modifications of the above processes are within the skill of one of ordinary skill in the art, and such modifications will not be described here.

However, we surprisingly found that a milling process using 0.5 mm high density zirconium silicate and more preferably 0.5 mm zirconia grinding media provides further efficient attrition, especially for the removal of particles greater than about 1 micron in the commercially available copper-based particulate product available from Phibro-Tech., Inc. The milling process usually takes on the order of minutes to achieve almost complete removal of particles greater than 1 micron in size. This wet milling process is inexpensive, and all of the precipitate can be used in the injectable copper-containing particulate wood treatment. The milling agents can be zirconia, partially stabilized zirconia, zirconium silicate, and yttrium/zirconium oxide, for example, recognizing that the more dense materials give faster particle size attrition. The size and density of the milling material is believed to be important, even critical, to obtaining a commercially acceptable process. The milling agent material having a diameter of 2 mm or greater are ineffective over hours and days, milling material of diameter of 1 mm is ineffective over times in the prior art, e.g., 10 minutes to an hour, while milling agent material having a diameter of 0.5 mm is effective typically after 15 minutes of milling.

We have surprisingly found that copper-based particulates that are manufactured by a straightforward precipitation process, using conditions known in the art to produce small particles, e.g., particles having a size less than 10 microns, can be readily milled into an injectable material. Therefore, milling other precipitate material with 0.5 mm diameter zirconium silicate (or any comparable product, e.g., a 0.3 mm to 0.7 mm sized zirconium silicate or zirconium oxide) can mill in a matter of minutes a substantially crystalline (or amorphous sparingly soluble) powder material having a larger initial average size into a product that can be readily injected into wood. Milling with 0.5 mm zirconium silicate and/or zirconia media not only quickly reduced further the magnesium stabilized copper hydroxide product, but this grinding medium was also found to be effective of other forms of basic copper compounds such as other stabilized copper hydroxides, copper carbonate, tribasic copper sulfate, copper oxychloride, and copper oxides, and also on solid organic biocides. The results of milling of a variety of materials with the 0.5 mm milling material described above for 15 minutes are shown in Table 2. Copper hydroxide material with an initial median size of 2.5 microns was quickly milled to an injectable material having a median particle size of 0.3 microns. Additional milling time would doubtless further reduce the median and average particle size. A copper carbonate material having a median size of 3.4 microns was milled to a material having a median size of less than 0.2 microns. FIG. 1 shows the face of wood injected with unmilled product and the face of wood injected with the milled product. In the color photographs the plugging is especially visible. A tribasic copper sulfate material having a median size of 6.2 microns was milled to a material having a median size of less than 0.2 microns in under 30 minutes. A copper oxychloride material having a median size of 3.3 microns was milled to a material having a median size of 0.4 microns.

Milling is believed to break up larger particles. It would also break particles having one large dimension, e.g., rod-like particles, which are know to have injection problems. Milling can be combined with for example centrifugation to create a more uniform product. Alternatively, milling can be combined with a coating process to form a more stable material.

In another preferred embodiment, slurry comprises a sparingly soluble copper salt particulates and also comprises zinc borate particulates. Preferably at least some of the sparingly soluble copper salt-based particulates comprise copper borate. It is known to use a two stage process where a zinc or copper salt is injected into the wood followed by a second step wherein the borax is injected and the insoluble metal borate is formed in situ. Such a complicated, time-consuming, and therefore expensive process in not sufficiently cost-effective. As the solubility of copper borate is very pH sensitive, in a preferred embodiment the sparingly soluble copper salts comprise an alkaline material, e.g., copper hydroxide or copper carbonate, to reduce the solubility of the copper borate.

In any of the above-described embodiments, the preservative can further comprise the substantially insoluble copper salt copper phosphate, $Cu_3(PO_4)_2$. Generally, in preferred embodiments, if $Cu_3(PO_4)_2$ is present it is a coating over other sparingly soluble copper salts, wherein the $Cu_3(PO_4)_2$ provides a fairly inert coating for a period of time before it dissolves or partially dissolves.

In any of the above-described embodiments, the preservative can further comprise the substantially insoluble copper salt copper phosphate, $Cu_3(PO_4)_2$. If there are copper-based-particulates substantially comprising $Cu_3(PO_4)_2$ and/or copper oxide, the particulates should be exceedingly small, e.g., less than about 0.05 microns, preferably less than about 0.04 microns, to provide maximum surface area to help dissolution of the particles, and the wood treatment should contain another type of substantially crystalline (or amorphous sparingly soluble) copper-based particulates, e.g., basic copper carbonate, copper borate, tribasic copper sulfate, copper hydroxides, and the like.

Basic copper phosphate is more preferred for the solid particulates, as it is more soluble and more bioactive than copper phosphate. Additionally, the phosphate ions can retard leaching of copper, neutralize acids in the wood, and in some instances help reduce corrosivity of the treated wood to metals. Mixtures of basic copper phosphate and basic copper sulfate are also useful, and they are often called basic copper phosphosulfate.

Conversely but advantageously, basic copper borate has a lower solubility than copper borate, which is advantageous because copper borate particles can dissolve fairly quickly, in terms of the expected life of a wood preservative. Basic copper borate has an advantage that the anion, borate, has advantageous biocidal and fire retarding properties.

As copper salts are millable and injectable, and organic biocides that are known to be difficult to mill are millable and injectable, there is no reason to doubt that organo-copper compiounds will also not be millable and injectable. In any of the embodiments, the preservative may comprise copper organic materials, especially those materials having a sparingly soluble partially crystalline nature, e.g., the ground copper organic salts disclosed in U.S. Pat. No. 4,075,326. In any of the above-described embodiments, the copper composition in copper-based particulates and/or copper-based particulate material can further comprise the substantially insoluble copper salt copper 8-quinolinolate. In any of the above-described embodiments, the composition can further comprise copper quinaldate, copper oxime, or both in particulate form. Its particularly noteworthy that organo-metallic materials, such as the copper salt of 8-hydroxyquinoline, copper oxime, and even traditionally oil-borne biocides such as copper naphthaenate, can now be milled into submicon injectable particles, and injected into and dispersed throughout wood, without use of dissolving oils. The zinc analogs are equally millable.

Preferred embodiments of the invention comprise particles comprising one or more of copper hydroxide, alkaline copper carbonate, alkaline copper oxychloride, tribasic copper sulfate, alkaline copper borate, basic copper phosphate, or mixtures thereof. The most preferred embodiments of the invention comprise particles comprising copper hydroxide, basic copper carbonate, basic copper borate, basic copper phosphate, or mixtures thereof.

Coatings for the Copper-Containing and Zinc-Containing Particulates.

In any of the above-described embodiments, the copper-containing particulates can further comprise one or more materials disposed on the exterior of the particles to inhibit dissolution of the underlying sparingly soluble copper material at least for a time necessary to prepare the formulation and inject the prepared wood treatment composition. Additionally or alternatively the acid-soluble particles are coated with a substantially inert coating, for example a thin outer coating of e.g. copper phosphate or copper sulfide, or a coating of a polymeric material such as dispersants and/or stabilizers, or with a thin hydrophobic coating of oil and/or of a liquid organic biocide, or any combination thereof. In one embodiment the particles are treated with a dispersing material which is substantially bound to the particles.

The milled organic and inorganic particles described above are readily slurried and injected into wood after the milling process. Generally, however, milling is done well before the particles are slurried and injected. The particles may be shipped in a dry form or in a wet form. The milled particles may be transported to a site as a dry mix or as a concentrated slurry, which is then formed into an injectable slurry, and then after some indeterminate storage time the particles may be injected into wood. Some particulates in solution have a tendency to grow over time. Others tend to agglomerate. Therefore, it is advantageous to have a coating on the particle to substantially hinder dissolution of the particle while the particle is slurried, and to make the particles substantially non-interacting and non-agglomerating. But, the coating should not overly hinder dissolution of the particle in the wood matrix.

Generally, the discussion focuses on the preferred copper-containing particulates, but the compositions and methods are equally applicable on the zinc-containing and tin-containing particulates. The sparingly soluble copper material, zinc material, and/or tin material can be stabilized by a partial or full coating of an inorganic salt. The manufacturing process is amenable to the formation of a substantially inert inorganic coating on the particle that will be of such low thickness that the coating will not substantially hinder particle dissolution in the wood. The preferred coatings are very low solubility metal salts of the underlying metal cations, e.g., copper, zinc, or tin. Exemplary very low solubility salts include copper sulfide (Ksp~$10^{-36}$), copper(II) phosphate (Ksp~$10^{-37}$), and copper 8-quinolinolate (Ksp~$10^{-30}$). The zinc and tin analogs are also very insoluble. The selection between sulfide, 8-quinolinolate, and phosphate generally depends on which coating shows the greatest protection for the particular substantially crystalline (or amorphous sparingly soluble) material, at the particular size distribution and particle morphology that may exist. A coating of a very low solubility salt can substantially arrest the dissolution/reprecipitation process by severely limiting the amount of copper that can dissolve. The coating, however, is mechanical protection only. Exposed portions of the underlying substantially crystalline (or amorphous sparingly soluble) copper-, zinc-, or tin-based particulates are subject to dissolution. Further, the inorganic coating is generally at most a few atoms to a few nanometers in depth.

The particles may be wet-milled using a very fine milling material and a fluid containing a source of phosphate ions, or less preferably (because of odor and handling problems) sulfide ions. In one preferred embodiment, the wet milling process uses as the milling fluid a composition comprising between a few hundred ppm of phosphate to about 6% phosphate, for example between 0.1% phosphate to 3% phosphate. Small amounts of phosphate will take hours or days to form a completely protective coating, while a more concentrated solution may form a protective coating in minutes. Advantageously the milling liquid has a pH between about 6 and about 9.5, for example between about 7 and about 8.5. This high concentration of phosphate is not wasteful because the milling fluid can be re-used, and also because the milling fluid is a relatively small volume. Such milling of particles of inorganic copper and inorganic zinc in the phosphate-containing milling fluid, for example for a time ranging from 5 minutes to 4 hours, typically from 10 minutes to 30 minutes, will promote the formation of a thin coating of copper(zinc) phosphate over the sparingly soluble copper material. As the coating is probably only a few atoms in thickness, the coating will dissolve in good time within the wood so as not to impair exposure of the underlying sparingly soluble copper material in the wood. Alternatively, a source of sulfide or 8-quinolinolate can be added to the milling liquid. Sulfide is again not preferred, for safety reasons.

In another embodiment, the copper-containing particles after milling can be exposed to a rinse solution that contains between a few hundred ppm of phosphate to about 6% phosphate, for example between 0.1% phosphate to 3% phosphate.

The invention also embraces embodiments where particles are substantially free of an inorganic coating.

Copper-containing particles, zinc-containing particles, tin-containing particles, and even solid substantially insoluble organic biocide particles may additionally comprise an organic coating, e.g., a organic layer that partially or completely covers the exterior surface area of the particulates. Indeed, in most preferred embodiments of the invention, the surface of the particles has bound thereto at least some dispersants and/or stabilizers, and these qualify as an organic covering. Generally such coatings are extremely thin, with a particulate comprising for example between about 0.1% to about 50% by weight, more typically from about 0.5% to about 10%, of the weight of the above-mentioned sparingly soluble salts. The coating may cover only a portion of the exterior surface area. The organic coating advantageously is a thin layer of organic material that at least partially coats the particulate and for a period of time reduces the tendency of the sparingly soluble copper, zinc, and/or tin salts in the particulates to dissolve in the slurry. This organic coating can comprise a variety of materials having a variety of functions over and above being an organic layer acting as a protective layer temporarily isolating the sparingly soluble salt from the aqueous carrier to slow dissolution of particulates in the slurry, including: 1) an organic biocide carrier, 2) dispersing/stabilizing agents, 3) wettability modifying agents, 3) substantially insoluble organic biocides, or any combinations thereof. The coating can comprise for example light oils, hydrophobic oils, and dehydrating oils; polymeric particles that are usually functionalized with for example carboxylate and or sulfonate moieties, organic biocides including for example an amine, azole, triazole, or any other organic biocides; dispersing agents and stabilizing agents/anti-coagulating agents including for example an organic compound having one or more polar functional groups which increase adherence, for example: mono- and/or poly-carboxylic acids that may be at least partially neutralized with a metal, or a film-forming polymer such as a sulfonated ionomer; a surfactant; amphoteric agents; or mixtures thereof. These and other organic and/or organometallic components that form an organic layer will generally be referred to as a "hydrocarbon layer" or "organic coating."

An organic coating comprising oils may be formed by contacting particulates with a hydrocarbon composition containing at least a portion of the materials to be deposited onto the exterior surface of the particle. The contacting may occur in a slurry or may be done with a paste of water-wetted particulates or may be done with dried particulates. The less free water, the easier it is to promote adherence between the hydrocarbon composition to the particulates. Drying oils and surface active agents such as stabilizers can also promote adherence of organic layer to the particle. Incorporating some solvents, typically polar solvents, e.g., at least 10%, for example at least 30% or at least 50% by weight of solvents such as one or more of alcohols, amides, ketones, esters, ethers, glycols, and such into the may help the hydrocarbon layer composition wet the particulates, and will allow thinner hydrocarbon layers to be deposited. Solvents are lower molecular weight and higher volatility than oils, and solvents may be stripped from the organic coating before slurrying the particles or during kiln drying of the wood. Advantageously, in one embodiment most of the solvent of the hydrocarbon composition is volatile and is removed prior to injection of the particulates into the wood. This will leave a thin layer of a more concentrated biocide in heavier oils and/or binders than was found in the hydrocarbon/biocide composition. The organic coating generally becomes more adherent if the coated particulates are allowed to age, and or are subjected to heat, for example to 35 C or above for a period of an hour, for example.

2) Surface-Active Agents—The surface active agents are advantageously included in the liquid while milling, and such agents are similarly useful in the product. The numerous stabilizers and dispersants listed in with respect to milling are included here by reference. Agents improving the suspension and dispersion of the particulates include dispersants such as phenyl sulfonates, alkylnaphthalene sulfonates and polymerized naphthalene sulfonates, polyacrylic acids and their salts, polyacrylamides, polyalkoxydiamine derivatives, polyethylene oxides, polypropylene oxide, polybutylene oxide, taurine derivatives and their mixtures, and sulfonated lignin derivatives. Surfactants include anionic surfactants, cationic surfactants, nonionic surfactants, or combinations thereof. Polyethyleneimine can act as a surfactant or a stabilizer and will also chelate copper. Dispersants can be used at 0.1% to 50%, preferably 0.5% to 20% or 5-10% of the particulate product.

Advantageously, if there are a plurality of types of particles in a slurry, the surface active dispersants and stabilizers are compatible and prevent the various types of particles from interacting or agglomerating.

3) Organic Biocides—As previously stated, the particles may be combined with one or more additional moldicides or more generally biocides, to provide added biocidal activity to the wood or wood products. The absolute quantity of organic biocides incorporated into most wood treatments is very low compared to the amount of inorganic salts, e.g., copper salts. In general, the biocides are present in a use concentration of from 0.1% to 20%, preferably 1% to 5%, based on the weight of the copper salts. The sparingly soluble copper-salt particulates of this invention are typically expected to be added to wood in an amount equal to or less than 0.25 pounds as copper per cubic foot. The organic biocide(s) at a 4% loading relative to the copper are present at about 0.16 ounces or about 3 to 4 milliliters of biocide per cubic foot. The organic biocides are often insoluble in water, which is the preferred fluid carrier for injecting the wood preservative treatment into wood, so getting adequate distribution of the biocide within the wood matrix is problematic. In prior art formulations, the wood preservative may be for example admixed in a large excess of oil, and the oil emulsified with water and admixed with the soluble copper for injection into the wood. Problems arise if the injection is delayed, or if the slurry has compounds which break the emulsion, and the like.

In one embodiment, a substantial benefit is that a portion or all of the organic biocides incorporated into the wood preservative treatment can advantageously be coated on to the particulates. Preferred preservative treatments comprise copper-based particles having one or more additional organic biocide(s) that are bound, such as by adsorption, to a surface of the particles. Wood and wood products may be impregnated substantially homogeneously with copper-based particles of the invention, each also comprising organic biocidal material bound to the surface of the copper-based particles. By substantially homogeneously we mean averaged over a volume of at least a cubic inches, as on a microscopic scale there will be volumes having particulates disposed therein and other volumes within the wood that do not have particulates therein. By adhering the biocides on particulates, a more even distribution of biocide in ensured, and the copper is disposed with the biocide and therefore is best positioned to protect the biocide from those bio-organisms which may degrade or consume the biocide. The homogenous distribution of preservative function within the wood or wood product is benefited. Finally, a formulation with biocide adhering to particulates does not face the instability problems that emulsions face during the formulation and injection phases.

Alternately or additionally, the organic biocide can be contained in milled injectable solid organic biocide particulates. Generally, such a small quantity of organic biocides are required that the $d_{50}$ of the organic biocides is advantageously between about 0.2 to about 0.8 times the $d_{50}$ of the sparingly soluble copper salts.

The biocides can be any of the known organic biocides. Exemplary materials having a preservative function include materials having at least one of one or more: azoles; triazoles; imidazoles; pyrimidinyl carbinoles; 2-amino-pyrimidines; morpholines; pyrroles; phenylamides; benzimidazoles; carbamates; dicarboximides; carboxamides; dithiocarbamates; dialkyldithiocarbamates; N-halomethylthio-dicarboximides; pyrrole carboxamides; oxine-copper, guanidines; strobilurines; nitrophenol derivatives; organo phosphorous derivatives; polyoxins; pyrrolethioamides; phosphonium compounds; polymeric quaternary ammonium borates; succinate dehydrogenase inhibitors; formaldehyde-releasing compounds; naphthalene derivatives; sulfenamides; aldehydes; quaternary ammonium compounds; amine oxides, nitrosoamines, phenol derivatives; organo-iodine derivatives; nitrites; quinolines such as 8-hydroxyquinoline including their Cu salts; phosphoric esters; organosilicon compounds; pyrethroids; nitroimines and nitromethylenes; and mixtures thereof Exemplary biocides include Azoles such as azaconazole, bitertanol, propiconazole, difenoconazole, diniconazole, cyproconazole, epoxiconazole, fluquinconazole, flusiazole, flutriafol, hexaconazole, imazalil, imibenconazole, ipconazole, tebuoonazole, tetraconazole, fenbuconazole, metconazole, myclobutanil, perfurazoate, penconazole, bromuconazole, pyrithiox, prochloraz, triadimefon, triadlmenol, triffumizole or triticonazole; pyrimidinyl carbinoles such as ancymidol, fenarimol or nuarimol; chlorothalonil; chlorpyriphos; N-cyclohexyldiazeniumdioxy; dichlofluanid; 8-hydroxyquinoline (oxine); isothiazolone; imidacloprid; 3-iodo-2-propynylbutylcarbamate tebuconazole; 2-(thiocyanomethylthio) benzothiazole (Busan 30); tributyltin oxide; propiconazole; synthetic pyrethroids; 2-amino-pyrimidine such as bupirimate, dimethirimol or ethirimol; morpholines such as dodemorph, fenpropidin, fenpropimorph, spiroxanin or tridemorph; anilinopyrimdines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprdine, myclozoline, procymidone or vinclozolin; carboxamides such as carboxin, fenfuram, flutolanil, mepronil, oxycarboxin or thifluzamide; guanidines such as guazatne, dodine or iminoctadine; strobilurines such as azoxystrobin, kresoxim-methyl, metominostrobin, SSF-129, methyl 2-[(2-trifluoromethyl)pyrid-yloxymethyl]-3-methoxycacrylate or 2-[α{[(.-methyl-3-trifluoromethyl-benzyl)imino]oxy}-o-tolyl]gly oxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluorormide, folpet or tolfluanid; nitrophenol derivatives such as dinocap or nitrothal-isopropyl; organo phosphorous derivatives such as edifenphos, iprobenphos, isoprothiolane, phosdiphen, pyrazophos or toclofosmethyl; and other compounds of diverse structures such as aciberolar-S-methyl, anilazine, blasticidin-S, chinomethionat, chloroneb, chlorothalonil, cymoxanil, dichlone, dicomezine, dicloran, diethofencarb, dimethomorph, dithianon, etridiazole, famoxadone, fenamidone, fentin, ferimzone, fluazinam, flusuffamide, fenhexamid, fosetyl-aluriinum, hymexazol, kasugamycin, methasuifocarb, pencycuron, phthalide, polyoxins, probenazole, propamocarb, pyroquilon, quinoxyfen, quintozene, sulfur, triazoxide, triciclazole, triforine, validamycin, (S)-5-methyl-2-methylthio-5-phenyl-3-phenyl-amino3,5-dihydroimidazol-4-one (RPA 407213), 3,5-dichloro-N-(3chloro-1-ethyl-1-methyl-2-oxopropyl)4-methylbenzamide (RH7281), N-alkyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042), or iprovalicarb (SZX 722). Also included are the biocides including pentachlorophenol, petroleum oils, phenothrin, phenthoate, phorate, as well as trifluoromethylpyrrole carboxamides and trifluoromethylpyrrolethioamides described in U.S. Pat. No. 6,699,818; Triazoles such as Amitrole, azocylotin, bitertanol, fenbuconazole, fenchlorazole, fenethanil, fluquinconazole, flusilazole, flutriafol, imibenconazole, isozofos, myclobutanil, metconazole, epoxyconazole, paclobutrazol, (±))-cis-1-(4-chlorophenyl)-2-(1H-1,2, 4-triazol-1-yl)-cycloheptanol, tetraconazole, triadimefon, triadimenol, triapenthenol, triflumizole, triticonazole, uniconazole and their metal salts and acid adducts; Imidazoles such as Imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide; azacanilide, bromuconazole, cyproconazole, dichlobutrazol, diniconazole, hexaconazole, metconazole, penconazole, epoxyconazole, methyl (E)-methoximino>α-(o-tolyloxy)-o-tolyl]acetate, methyl (E)-2-{2→6-(2-cyanophenoxy)-pyrimidin-4-yl-oxy!phenyl}-3-methoxyacrylate, methfuroxam, carboxin, fenpiclonil, 4(2,2-difluoro-1,3-benzodioxol-4-yl)-1H-pyrrole-3-carbonitrile, butenafine, 3-iodo-2-propinyl n-butylcarbamate; triazoles such as described in U.S. Pat. Nos. 5,624,916; 5,527,816; and 5,462, 931; the biocides described in U.S. Pat. No. 5,874,025; 5-[(4-chlorophenyl)methyl]-2,2-dimethyl-1-(1H-1,2,4-triazol-1-yl-methyl)cyclopentanol and imidacloprid, 1-[(6-chloro-3-pyridinyl)-methyl]-4,5-dihydro-N-nitro-1H-imidazole-2-amine; Methyl(E)-2→2→6-(2-cyanophenoxyl)pyrimidin-4-yloxy!phenyl!3-methoxyacrylat e, methyl(E)-2→2→6-(2-thioamidophenoxyl)pyrimidin-4-yloxyl!phenyl!-3-methoxyacrylate, methyl(E)-2→2→6-(2-fluorophenoxyl)pyrimidin-4-yloxy!phenyl!-3-methoxyacry late, methyl(E)-2→2→6-(2,6-difluorophenoxyl)pyrimidin-4-yloxy!phenyl!-3-methoxy acrylate, methyl(E)-2→2→3-(pyrimidin-2-yloxy) phenoxy!phenyl!-3-methoxyacrylate, methyl(E)-2→2→3-(5-methylpyrimidin-2-yloxy)-phenoxy!phenyl!-3-methoxyacrylate, methyl(E)-2→2→3-(phenylsulphonyloxy) phenoxy!phenyl-3-methoxyacrylate, methyl(E)-2→2→3-(4-nitrophenoxyl)phenoxy!phenyl!-3-methoxyacrylate, methyl(E)-2→2-phenoxyphenyl-3-methoxyacrylate, methyl (E)-2→2-(3,5-dimethylbenzoyl)pyrrol-1-yl-3-methoxyacrylate, methyl(E)-2→2-(3-methoxyphenoxyl)phenyl!-3-methoxyacrylate, methyl(E)-2>2-(2-phenylethen-1-yl)-phenyl-3-methoxyacrylate, methyl(E)-2→2-(3,5-dichlorophenoxyl) pyridin-3-yl!-3-methoxyacrylate, methyl(E)-2-(2-(3-(1,1,2, 2-tetrafluoroethoxyl)phenoxy)phenyl)-3-methoxyacry late, methyl(E)-2-(2→3-(alphahydroxybenzyl)phenoxy!phenyl)-3-methoxyacrylate, methyl(E)-2-(2-(4-phenoxypyridin-2-yloxy)phenyl)-3-methoxyacrylate, methyl(E)-2→2-(3-n-propyloxyphenoxy)phenyl3-methoxyacrylate, methyl(E)-2→2-(3-isopropyloxyphenoxyl)phenyl!-3-methoxyacrylate, methyl(E)-2→2→3-(2-fluorophenoxyl)phenoxy!phenyl!-3-methoxyacrylate, methyl(E)-2→2-(3-ethoxyphenoxyl)phenyl-3-methoxyacrylate, methyl(E)-2→2-(4-tert-butylpyridin-2-yloxy)phenyl!-3-methoxyacrylate; Fenfuram, furcarbanil, cyclafluramid, furmecyclox, seedvax, metsulfovax, pyrocarbolid, oxycarboxin, shirlan, mebenil (mepronil), benodanil, flutolanil; Benzimidazoles, such as carbendazim, benomyl, furathiocarb, fuberidazole, thiophonatmethyl, thiabendazole or their salts; Morpholine derivatives, such as tridemorph, fenpropimorph, falimorph, dimethomorph, dodemorph; aldimorph, fenpropidine and their arylsulphonates, such as, for example, p-toluenesulphonic acid and p-dodecylphenylsulphonic acid; Benzothiazoles, such as 2-mercaptobenzothiazole; Benzam ides, such as 2,6-dichloro-N-(4-trifluoromethylbenzyl)-benzamide; oxazolidine, hexa-hydro-S-triazines, N-methylolchloroacetamide, paraformadehyde, nitropyrin, oxolinic acid, tecloftalam; Tris-N-(cyclohexyldiazeneiumdioxy)-aluminium, N-(cyclohexyldiazeneiumdioxy)-tributyltin, N-octyl-isothiazolin-3-one,4,5-trimethylene-isothiazolinone, 4,5-benzoisothiazolinone, N-methylolchloroacetamide; Pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropane-carboxylate, fenpropathrin, fenfluthrin, fenvalerate, flucythrinate, flumethrin, fluvalinate, permethrin, resmethrin and tralomethrin; Nitroimines and nitromethylenes, such as 1→(6-chloro-3-pyridinyl)-methyl!-4,5-dihydro-N-nitro-1H-imidazol-2-amine (imidacloprid), N→(6-chloro-3-pyridyl)methyl-!N$^2$-cyano-N$^1$-methylacetamide (NI-25); Quaternary ammonium compounds, such as didecyldimethylammonium salts; benzyldimethyltetradecylammonium chloride, benzyldimethyldodecylammonium chloride, didecyldimethaylammonium chloride; Phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts; iodine derivatives, such as diiodomethyl p-tolyl sulphone, 3-iodo-2-propinyl alcohol, 4-chloro-phenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; Microbicides having an activated halogen group, such as chloroacetamide, bronopol, bronidox, tectamer, such as 2-bromo-2-nitro-1,3-propanediol, 2-bromo-4'-hydroxy-acetophenone, 2,2-dibromo-3-nitrile-propionamide, 1,2-dibromo-2,4-dicyanobutane, β-bromo-.-nitrostyrene; and combinations thereof. These are merely exemplary of a few classes of the known and useful biocides, and the list could easily extend for pages.

Preferred biocides for wood preservation include quaternary ammonium compounds including for example didecyldimethylammonium salts; azoles/triazoles including for example N-alkylated tolytriazoles, metconazole, imidacloprid, hexaconazole, azaconazole, propiconazole, tebuconazole, cyproconazole, bromoconazole, and tridemorph tebuconazole; moldicides; HDO available commercially by BASF, or mixtures thereof.

Exemplary millable biocides include Chlorothalonil, Metaldehyde, triphenyltin hydroxide, Maneb, Mancozeb, Zineb, Ziram, and/or Ferbam, and wherein the milled organic biocide product preferably has a volume mean diameter $d_{50}$ between about 0.1 and 0.3 microns and a $d_{90}$, such that 90 volume percent of the product has a diameter of the d90 or less, of less than about 3 times the $d_{50}$.

Generally, millable biocides can be found in each of imidazolinones, sulfonylureas, triazolopyrimidine sulfonamides, aryloxyphenoxy propionates, triazines, chloroacetanilides, pyrazoles, and diphenyl ethers. Specific examples of millable biocides, some of which are useful for wood preservative applications and some of which are useful in foliar applications, include amitraz, azinphos-ethyl, azinphos-methyl, benzoximate, fenobucarb, gamma-HCH, methidathion, deltamethrin, dicofol, dioxabenzafos, dioxacarb, dinobuton, endosulfan, bifenthrin, binapacryl, bioresmethrin, chlorpyrifos, chlorpyrifos-methyl, EPNethiofencarb, cyanophos, cyfluthrin, tetradifon, cypermethrin, tralomethrin, bromophos, N-2,3-dihydro-3-methyl-1,3-thiazol-2-ylidene-xylidene, 2,4-parathion methyl, bromopropylate, butacarboxim, butoxycarboxin, chlordimeform, phosalone, chlorobenzilate, phosfolan, chloropropylate, phosmet, chlorophoxim, promecarb, fenamiphos, quinalphos, resmethrin, temephos, pirimiphos-ethyl, tetramethrin, pirimiphos-methyl, xylylcarb, profenofos, acrinathrin, propaphos, allethrin, propargite, benfuracarb, propetamphos, bioallethrin, pyrachlofos, bioallethrin S, tefluthrin, bioresmethrin, terbufos, buprofezin, tetrachlorinphos, chlorfenvinphos, tralomethrin, chlorflurazuron, triazophos, chlormephos, pyrachlofos, tefluthrin, terbufos, tetrachlorinphos, cycloprothrin, betacyfluthrin, cyhalothrin, cambda-cyhalothrin, tralomethrin, alpha-cypermethrin, triazophos, beta-cypermethrin, cyphenothrin, demeton-S-methyl, dichlorvos, disulfoton, edifenphos, empenthrin, esfenvalerate, ethoprophos, etofenprox, etrimphos, fenazaquin, fenitrothion, fenthiocarb, fenpropathrin, fenthion, fenvalerate, flucythrinate, flufenoxuron, tau-fluvalinate, formothion, hexaflumuron, hyoprene, isofenphos, isoprocarb, isoxathion, malathion, mephospholan, methoprene, methoxychlor, mevinphos, permethrin, phenothrin, phenthoate, benalaxyl, biteranol, bupirimate, cyproconazole, carboxin, tetraconazole, dodemorph, difenoconazole, dodine, dimethomorph, fenarimol, diniconazole, ditalimfos, ethoxyquin, myclobutanil, etridiazole, nuarimol, fenpropidin, oxycarboxin, fluchloralin, penconazole, flusilazole, prochloraz, imibenconazole, tolclofos-methyl, myclobutanil, triadimefon, propiconazole, triadimenol, pyrifenox, azaconazole, tebuconazole, epoxyconazole, tridemorph, fenpropimorph, triflumizole, 2,4-D esters, diclofop-methyldiethatyl, 2,4-DB esters, dimethachlor, acetochlor, dinitramine, aclonifen, ethalfluralin, alachlor, ethofumesate, anilophos, fenobucarb, benfluralin, fenoxapropethyl, benfuresate, fluazifop, bensulide, fluazifop-P, benzoylpropethyl, fluchloralin, bifenox, flufenoxim, bromoxynil esters, flumetralin, bromoxynil, flumetralin, butachlor, fluorodifen, butamifos, fluoroglycofen ethyl, butralin, fluoroxypyr esters, butylate, carbetamide, chlornitrofen, chlorpropham, cinmethylin, clethodim, clomazone, clopyralid esters, CMPP esters, cycloate, cycloxydim, desmedipham, dichlorprop esters, flurecol butyl, fluorochloralin, haloxyfop, ethoxyethyl, haloxyfop-methyl, ioxynil esters, isopropalin, MCPA esters, mecoprop-P esters, metolachlor, monalide, napropamide, nitrofen, oxadiazon, oxyfluorfen, pendimethalin, phenisopham, phenmedipham, picloram esters, pretilachlor, profluralin, propachlor, propanil, propaquizafop, pyridate, quizalofop-P, triclopyr esters, and tridiphane.

Of course, organic biocides can be coated onto ground organic particulates in much the same manner that they can be coated onto inorganic salt particles. This ability allows a formulator to include for example a primary organic biocide and one or more secondary organic biocides on the same particle. This is particularly advantageous if the secondary biocides are targeted specifically toward one or more bio-organisms that degrade the primary biocide.

It can be seen that the ability to formulate very small particulates, and to optionally coat these particulate with biocides as well as with stabilizers and dispersants, opens a wide variety of possibilities for the use of biocides in the fields of foliar applications, wood preservation, antifouling paints and coatings, and even biocidal coverings such as roofs and walls. Generally, the differences between foliar applications and wood preservatives are: the foliar applications are subject to more UV light and greater water flux; foliar applications are typically not intended to have a lifetime greater than one year, while wood preservative treatments try to attain 20 or more year lifespans, and the particle size distribution in wood preservation must be much narrower, particularly on the upper end of the particle size distribution.

For foliar and for wood preservative applications, a slurry composition is preferred, for example a slurry comprising: a liquid carrier comprising stabilizers and dispersants; and one or more of:

1) injectable solid particulates comprising a substantially insoluble solid organic biocide;

2) injectable solid particulates comprising a substantially insoluble solid organic biocide and coated with a thin organic layer which may comprise a substantially insoluble organic biocide;

3) injectable solid particulates comprising a sparingly soluble copper salts;

4) injectable solid particulates comprising a sparingly soluble copper salts and coated with a thin organic layer which may comprise a substantially insoluble organic biocide;

5) injectable solid particulates comprising a sparingly soluble zinc (and/or tin) salts;

6) injectable solid particulates comprising a sparingly soluble zinc (and/or tin) salts and coated with a thin organic layer which may comprise a substantially insoluble organic biocide; inert carrier particles coated with a organic layer comprising a substantially insoluble organic biocide, and optionally but disfavored a soluble copper amine.

The inert carrier particulates can be bioactive zeolite-based particles, alumina particles, and the like. An exemplary particle comprises copper hydroxide having an average particle diameter of less than about 500 nanometers, for example less than about 250 nanometers, or less than about 200 nanometers, as measured by Stokes Law settling velocity. Preferably, the average particle diameter is at least 25 nanometers, for example, at least 50 nanometers. The particle size distribution of the particulates in one embodiment is such that at least about 30% by weight of the particulates have an average diameter between about 0.07 microns and about 0.5 microns, or preferably at least about 50% by weight of the particulates have an average diameter between about 0.1 microns and about 0.4 microns.

The particle size distribution of the particulates in one embodiment is such that at least about 30% by weight of the particulates have an average diameter between about 0.02 microns and about 0.4 microns, or preferably at least about 50% by weight of the particulates have an average diameter between about 0.05 microns and about 0.3 microns. The metallic copper and/or metallic zinc particulates have both a minor biocidal effect and also an anti-corrosion effect. The amount of metal, either copper, zinc, or both, in the anti-corrosion metallic particulates can range from about 1 part to about 25 parts per 100 parts of particulates comprising slightly soluble copper salts. The metal-containing particulates in this variant of the invention are primarily anti-corrosion additives, though they will have some biocidal effect. Further, organic biocides can be readily coated onto these metal-containing particulates.

In a preferred embodiment the sparingly soluble copper salts in the copper-containing particulates comprise or consist essentially of one or more copper salts selected from copper hydroxides; copper carbonates, basic (or "alkaline") copper carbonates; basic copper sulfates including particularly tribasic copper sulfate; basic copper nitrates; copper oxychlorides (basic copper chlorides); basic copper sulfates, basic copper borates, and mixtures thereof. In one embodiment, the copper-based particles comprise a substantially crystalline copper compound. At least about 20%, 30%, 50%, or 75% of the weight of the copper-based particles may be composed of the substantially crystalline copper compound.

The zinc analogs of the above are useful for the zinc-based particulates of the alternate embodiments of the invention. In one embodiment the copper-based particulate material can further comprise one or more of crystalline zinc salts selected from zinc hydroxide; zinc oxides; zinc carbonate; zinc oxychloride; zinc fluoroborate; zinc borate, zinc fluoride, or mixture thereof.

In preferred embodiments of this invention, the slurry is substantially free of alkanolamines, e.g., the slurry comprises less than 1% alkanolamines, preferably less than 0.1% alkanolamines, or is totally free of alkanolamines.

In preferred embodiments of this invention, the slurry is substantially free of amines, e.g., the slurry comprises less than 1% amines, preferably less than 0.1% amines, or is totally free of amines, with the proviso that amines whose primary function is as an organic biocide are excluded. Generally, if amines are included, they form dispersants and stabilizers, and they are used at the lowest practicable concentrations.

In preferred embodiments of this invention, the slurry is substantially free of ammonium compounds (e.g., ammonium hydroxide), e.g., the slurry comprises less than 1% ammonia, preferably less than 0.1% ammonia, or is totally free of ammonium compounds, with the proviso that ammonium compounds whose primary function is as an organic biocide are excluded.

In preferred embodiments of this invention, the slurry is substantially free of solvents, e.g., the slurry comprises less than 1% organic solvents, preferably less than 0.1% organic solvents, or is totally free of organic solvents.

The loading of the particulates in the slurry will depend on a variety of factors, including the desired copper loading in the wood, the porosity of the wood, and the dryness of the wood. Calculating the amount of copper-based particulates and/or other particulates in the slurry is well within the skill of one of ordinary skill in the art. Generally, the desired copper loading into wood is between 0.025 and about 0.5 pounds copper per cubic foot of wood.

In a preferred embodiment the liquid carrier consists essentially of water and optionally one or more additives to aid particulate dispersion, pH maintenance, interfacial tension (surfactants), and particle stability (anticoagulants). In another embodiment the carrier consists essentially of water and optionally one or more additives to aid particulate dispersion, pH maintenance, interfacial tension, stabilizers/anticoagulants, and oil-in-water emulsion of oil containing organic biocides dissolved therein.

Advantageously the pH of the liquid carrier is between about 7 and about 11, for example between about 7.5 to about 9, or between about 8 and about 8.5. Alternately, the pH of the injectable slurry is between pH 6 and 11, preferably between 7 and 10, for example between 7.5 and about 9.5. Acidic pH slurries are not preferred because several of the sparingly soluble copper salts of this invention have a higher solubility at lower pH. The pH can be adjusted with alkali hydroxides, alkali carbonates, less preferably with alkaline earth oxides or hydroxides; and even less preferably with amines including ammonium hydroxide. Alkaline earth bases are less preferred because if carbon dioxide or carbonates are present in solution, there is a possibility of precipitation, for example of calcite. Such precipitation may create undesired plugging of the wood during injection. The preferred ingredients to increase the pH is an alkali hydroxide, e.g., sodium hydroxide or potassium hydroxide or alkali carbonate, or both.

It may be advantageous to add basic alkali phosphate, basic alkali borate, or the monoacid forms thereof, or any combinations thereof, to the liquid carrier to increase the pH and provide some buffering capacity. The slurry is beneficially buffered, by for example adding phosphate at 5 ppm to 500 ppm. The higher concentrations of phosphates may be beneficial if the particulates do not have any coatings formed thereon, as the soluble phosphate ions will discourage dissolution of the copper salts from the particulates into the liquid carrier. Soluble borates can be added in an amount from about 5 ppm to about 2000 ppm in the slurry, where less than 5 ppm has little effect and more than 2000 ppm is cost-prohibitive. Borates have both a biocidal activity and a fire-retardant activity.

In one embodiment the slurry comprises between 50 and 800 ppm of one or more scale precipitation inhibitors, particularly organophosphonates. Alternately or additionally the slurry may contain between about 50 and about 2000 ppm of one or more chelators. Both of these additives are meant to inhibit precipitation of salts such as calcium carbonate and the like, where the source of calcium may be from the water used to make up the slurry. The preferred inhibitors are hydroxyethylidene diphosphonic acid (HEDP), diethylenetriamine-pentamethylenephosphonic acid (DTPMP), and/or 2-phosphonobutane-1,2,4-tricarboxylic acid (PBTC). If the preservative is in a slurry concentrate, the slurry should comprise between 10 mmoles and 100 mmoles/L of HEDP, or between 30 mmoles and 170 mmoles/L of PBTC or DTPMP. Mixtures of inhibitors are preferred, as concentrates may have more inhibitor than can readily be solubilized therein. If the preservative is in a solid form, the preservative should comprise between about 0.1 to about 1 mole HEDP per kg of particulates, or between about 0.17 to about 2 mole PBTC and/or DTPMP per kg of particulates.

Increased corrosion of metal fillings has been observed in formulations using soluble copper preservatives, as opposed to the prior art CCA formulations. The slurry of this invention, having a basic pH and having very low amine content, is expected to reduce the corrosion rate over that seen with soluble copper. There are additional treatment that can help reduce corrosion. The presence of phosphate salts in both the inorganic sparingly soluble particulates of some embodiments of the invention, and also optionally dissolved in the liquid phase of the slurry, is expected to reduce corrosion. The presence of carbonates and hydroxides, in both the inorganic sparingly soluble particulates of preferred embodiments of the invention, and also optionally dissolved in the liquid phase of the slurry, is expected to reduce corrosion. Eliminating amines, especially the large quantity of amines complexed with the copper in currently used formulations, is expected to reduce corrosion and mold.

Preferred preservative materials inhibit organisms that may be resistant to copper-based preservatives. Moldicides useful in wood or wood product preservation are also preferred organic biocides. If the wood preservative treatment will comprise substantially insoluble organic biocides, these substantially insoluble organic biocides may be partially or fully coated onto the milled injectable sparingly soluble copper-containing particulates, sparingly soluble zinc-containing particulates, sparingly soluble tin-containing particulates, or mixtures thereof. The substantially insoluble organic biocides may alternatively or additionally be present as milled, injectable particulates independent of the milled injectable inorganic salt particulates. Substantially insoluble organic biocides may be coated on a milled injectable particle of a different organic biocide. Alternatively or additionally, these biocides may be partially or fully coated onto the available surface area of an inert particulate carrier. Alternatively, the organic biocides can be placed in a oil in water emulsion and injected as in the prior art, and a portion of the emulsion will end up coating particles.

The slurry can advantageously contain one or more additives to aid wetting, for example surfactants. Surfactants may be in solution, or alternatively may bind to the surface, in which case they are surface-active agents and may function as stabilizers or dispersants. Preferred dispersing agents include a surface active portion that interacts with the copper-containing particle and a second preferably different portion, which operates to inhibit irreversible agglomeration of the copper-based particles. For example, a polyacrylate dispersing agent may include at least one carboxyl group capable of associating, such as electrostaticaly, with a copper-containing particle and a second, hydrophobic portion that may operate to inhibit the permanent agglomeration of the copper-containing particles. Exemplary dispersing agents may include at least one of a surfactant, a polyacrylate, a polysaccharide, a polyaspartic acid, a polysiloxane, and a zwitterionic compound. Exemplary compounds useful as dispersing agents are discussed in the section relating to milling.

In one embodiment of the invention, the copper-based particles may comprise a polymer. In this embodiment, the ratio of the weight of copper present in the particles to polymer present in the particles may be at least about 1 to 1, for example at least about 2 to 1, 4 to 1, 5 to 1, 7 to 1, or at least about 10 to 1. For example, if ratio of the weight of copper present in the particles to the weight of polymer present in the particles is at least about 2 to 1, the particles comprise at least about twice as much copper by weight as polymer. Another aspect of the invention relates to a preservative useful for wood or wood products, the preservative preferably comprising a preferably aqueous suspension of copper-based particles. If a polymeric dispersing agent is present in the suspension, the ratio of the weight of copper present in the copper-based particles of the suspension to the weight of dispersing agent present in the suspension may be at least about 1 to 1, for example at least about 5 to 1, 10 to 1, 15 to 1, 20 to 1 or at least about 30 to 1.

Dispersing agents aid particulate dispersion and to prevent aggregation of particulates. Sub-micron sized particulates have a tendency to form much larger aggregates. Aggregates as used herein are physical combinations of a plurality of similarly-sized particles, often brought together by VanDerWaal's forces or electrostatic forces. If aggregates are allowed to form they often can age into a stable aggregate that can not be readily broken up by mechanical agitation, for example by vigorous stirring of a slurry. Such aggregates may grow to a size where the aggregates are not readily injectable, or may be of a size to make the aggregates visible, therefor giving undesired color. In preferred embodiments of the invention at least 30%, preferably at least 60%, more preferably at least 90% by weight of the substantially crystalline copper-based particulates in a slurry are mono-disbursed, e.g., are not in aggregates. Further, the particles advantageously do not tend to agglomerate when injected into the wood. To prevent particulates from agglomerating, the concentrated slurry or paste may comprise cationic, anionic, and/or nonionic surfactants; emulsifiers such as gelatine, casein, gum arabic, lysalbinic acid, and starch; and/or polymers, such as polyvinyl alcohols, polyvinyl pyrrolidones, polyalkylene glycols and polyacrylates, in quantities of 0.1 to 20% by weight, based on the weight of the particulates.

The slurry formulations mentioned can be prepared in a manner known per se, for example by mixing the active compounds with the liquid carrier, and including emulsifier, dispersants and/or binders or fixative, and other processing auxiliaries. Particulates can be provided in a concentrated slurry, in a very concentrated paste, as dry particulates, as coated dry particulates, as part of a dry pre-mix, or any combination thereof.

Slurry Concentrate—If the wood treatment is to be manufactured, stored, or transported in a wetted form, it is beneficially in a concentrated form to minimize the volume and expense of handling water. Preferably the concentrated slurry or paste (for shipping and storing, for example, comprises between 5% and 80% by weight, for example between about 15% and 40%, of sparingly soluble copper-containing particulates, sparingly soluble zinc-containing particulates, sparingly soluble tin-containing particulates, or mixtures thereof, optionally with 0.1% to 10% of particulates of organic biocides, with the remainder of the concentrated slurry or paste beneficially being a fluid carrier. The concentrated slurry or paste may further comprise solid particulates that are carriers for one or more organic biocides, solid particulates comprising metallic copper and/or zinc as corrosion inhibitors, or both. The fluid carrier beneficially comprises one or more additives as discussed for the slurry, including anti-oxidants, surfactants, disbursing agents, other biocidal salts and compounds, chelators, corrosion inhibitors, e.g., phosphate and/or borate salts, alkali metal hydroxides and/or carbonates, antifreeze, and the like. The concentration of these additives will depend in part on the degree to which the slurry is expected to be diluted to make a commercially useful injectable slurry having the proper copper loading for the types of wood.

The moisture content of copper-based particles of the invention may be reduced, such as by drying. one or more dispersing agents may be used to inhibit irreversible agglomeration of reduced moisture particles of the invention. The reduced moisture particles may be diluted, such as by hydration with water or combination with another liquid. Generally, dilution may be with water, beneficially fresh water.

Another aspect of the invention relates to an agglomeration comprising a plurality of copper-containing particles, organic biocide-containing particles, or both, and dispersing agents. The agglomeration may also include one or more materials additional to the copper-based particles that also provide a wood or wood product preservative function. The agglomeration may have a liquid content (excluding any additional preservative material that may be present) of less than 75% by weight, for example, of less than about 50%, less than about 25%, less than about 15%, or less than about 5% by weight. The liquid may be water. The agglomeration may be diluted and/or dispersed in water with mixing or agitation, such as mechanically or ultrasonically.

As in the injectable slurry itself, the $d_{99}$, and preferably the $d_{99.5}$, should be less than 1 micron, more preferably less than about 0.6 microns. Advantageously the at least about 30% by weight of the particulates have an average diameter between about 0.07 microns and about 0.5 microns. In a preferred embodiment, at least about 50% by weight of the particulates have an average diameter between about 0.1 microns and about 0.4 microns.

Dry Particulates and Dry Mix For Slurry—The particulates of this invention can be formulated and transported as a dry material, e.g., as a wettable powder, as dispersible granules, and even as larger tablets. The wettable powder, dispersible granules, or tablets advantageously comprise the biocidal particulates and those additives such as are described as being present in the slurry, including for example anti-oxidants, surfactants, disbursing agents/stabilizing agents, chelators such as salts of ETDA, basic compounds, sequestrants such as salts of HEDP, and the like. The additives can be coated onto the sparingly soluble copper-based particulates and/or can be formed from second particulates. The dry-mix material advantageously has all necessary components in a single mix, and each component is present in a range that is useful when the dry mix is formed into a sprayable or injectable slurry. The mixture may optionally but preferably incorporate a granulating material, which is a material that when wet holds a plurality of particulates together in the form of a granule or tablet, but that dissolves and releases the individual particulates on being admixed with the liquid carrier. Granules are preferred because of dust problems and also the ease of measuring and handling a granular mixture. Granulating agents can be simple soluble salts, for example alkali carbonates, that are sprayed onto or otherwise is admixed with the particulate material.

One example of a biocide composition in granular or tablet form, which rapidly disintegrates and disperses in water, includes, e.g., about 50 parts particulate biocide, about 10 to about 40 parts salts, preferably carbonate and/or bicarbonate salts, about 1 to about 20 parts solid chelators/sequestrants, about 5 to about 50 parts stabilizers and/or dispersants, and up to about 20 parts filler. Another exemplary dissolvable biocide granule comprises: 1) about 50-75% of a first finely-divided (submicron) particulate biocides, which may be a biocidal inorganic sparingly soluble copper salt, such as is produced by the processes of this invention; 2) optionally about 7-15% of a second particulate biocide, which may include particulates of solid essentially water-insoluble organic biocide; 3) about 2-30% of a stabilizer and/or dispersing agent; 4) about 0.01-10% of a wetting agent; 5) about 0-2% of an antifoaming agent; 6) about 0-5% of a diluent; and optionally 7) about 0-5% of a chelating agent. One embodiment of the invention relates to a dry mix material having a copper content of at least about 8% by weight. A preferred material includes a plurality of copper-containing particles. The material may be shipped, such as in granular form, to a location at which the material is prepared for use a wood preservative. The material may also comprise at least one of a wetting agent, a dispersing agent, a diluent which may be a particulate comprising organic biocides thereon, an antifoaming agent, and an additional material having a biocide function.

One embodiment of the invention relates to a dry material having a copper content of at least about 15% by weight. A preferred material includes a plurality of copper-containing particles, which may be in the form of granules. The material also comprises at least one of a wetting agent, a dispersing agent, a diluent, an antifoaming agent, and an additional material having a biocide function. In one embodiment, the material is a granular material comprising about 50% to 70%, for example 58% copper hydroxide or other sparingly soluble copper salts, about 10% to 25%, for example 18% of a dispersing agent, such as Borrespersse NA, about 1 to 8%, e.g., about 4% of a wetting agent, such as Morwet EP, and about 10% to about 30% filler, e.g., about 20% attapulgite clay, such as Diluex A; optionally from 0.05% to 7% alkali hydroxides, alkali carbonates, alkali phophates, and/or alkali borates; optionally 0.05% to 5% salts of a sequestrant, for example HEDP, and optionally from 0.05% to 2% antifoaming agents.

In one embodiment, the dry-mix material is a granular material comprising about 40 to about 80% by weight of a sparingly soluble copper salt, e.g., copper hydroxide, about 5% to about 30% of a dispersing agent, such as Borresperse NA, about 1% to about 10% of a wetting agent, such as Morwet EP, and about 5% to about 30% of a inert particulate filler which may additionally comprise organic biocides absorbed thereon, e.g., attapulgite clay, such as Diluex A. In one embodiment, the material is a granular material comprising about 58% copper hydroxide, about 18% of a dispersing agent, such as Borresperse NA, about 4% of a wetting agent, such as Morwet EP, and about 20% attapulgite clay, such as Diluex A.

Another aspect of the invention relates to material comprising a copper content of at least about 15%, for example, at least about 20%, such as at least about 30% by weight. In one embodiment, the material may have a copper content of about 35% by weight. The material may have a copper content of less than about 50%, for example, less than about 45%, such as less than about 40% by weight. Preferably, the material comprises a plurality of copper-based particles, which may contribute substantially all of the copper content of the material. The material may comprise a plurality of granules each comprising a plurality of copper-based particles. The copper-based particles, such as a surface thereof, may be associated with a dispersing agent.

In one embodiment, the material comprises A) about 30% to 70% by weight of a slightly soluble copper salt, e.g., copper hydroxide, for example, about 35% to 65%, such as about 38% to about 61% of a slightly soluble copper salt, in particulate form; B) about 10% to 35% by weight, such as about 15% to about 30% of at least one dispersing agent, e.g., lignosulfonates or polyacrylates; C) between about 2.5% to 20% by weight, such as about 5% to 15% of at least one wetting agent, for example, a surfactant, e.g., Morwet EP available from Barton Solvents, Inc.; D) between about 5% to about 25% by weight, such as about 10% to 20% of at least one diluent, for example soluble and insoluble diluents, such as those used in agricultural products, e.g., clay, such as an attapulgite clay, or particulate carrier particles comprising organic biocide; E) between about 0.05% to 7.5% by weight, such as about 0.1% to about 5%, of at least one antifoam agent; and optionally F) about 2.5% to about 25%, alternatively less than about 7.5%, such as less than about 5% by weight, of water.

The material may be shipped, such as in granular form. The material of the invention offers reduced shipping costs and improved ease of handling compared to known preservative materials. A user may receive the material and, if granules are present, disperse the granules, thereby preparing a flowable material comprising a plurality of copper-based particles. The material may be diluted, for example by using water or other liquid. The copper-based particles may be injected into wood and/or wood materials as a preservative. Mechanical agitation and/or mixing may be used to disperse the granules.

Upon dispersing the material, wood or wood products may be treated with the dispersed material, such as by subjecting the wood or wood products to vacuum and or pressure in the presence of the dispersed material. Upon dispersing granules of the material, dispersed copper-based particles preferably remain suspended for at least about 30 minutes without further agitation, preferably, even in standard hard water having a hardness of about 342 ppm. Once dispersed, fifty percent of the dispersed copper-based particles may have diameters less than about 1 micron, for example, less than about 0.5 micron, such as less than about 0.25 micron. In one embodiment, 50% of the dispersed copper-based particles have diameters less than about 0.2 micron, for example, 50% of the dispersed copper-based particles have diameters of about 0.1 micron.

The copper-based material may comprise additional material providing a wood preservative and/or biocide function. For example, in one embodiment the material comprises a plurality of copper-based particles and a co-biocide. Exemplary organic co-biocides may include, for example, one or more of a triazole compound, a quarternary amine, and a nitroso-amine.

One object of the invention is to provide an effective, injectable copper-based particulate preservative treatment that has leaching characteristics lower than copper amine treatments. Generally, leach rate tests involve high leachant rates so the leachant can not equilibrate with the sparingly soluble salts, and therefore measured leach rates from particulates are expected to be low compared to leach rates from more quiescent systems. By "leach rate less than for copper amine treatment" we mean the leach rate using the AWPA test, determined as percent of copper leached versus hours in wood samples, where one wood sample has the slurry of this invention and the comparative wood sample has a similar total copper loading from injected copper monoethanolamine carbonate formulations, at 240 hours using the preferred method of measuring leaching is with the AWPA Standard Method E11-97 (1997), using a test extending to at least 300 hours duration. Another object of the invention is to provide an effective, injectable copper-based particulate preservative treatment that retains more than 94% of copper injected in a 14 day standard leach test.

Advantageously the copper-based particulate is an effective preservative. To be effective, the copper-based particles comprise one or more sparingly soluble copper salts, and these salts must together release a small but effective concentration of soluble copper when wetted with water. If the copper salts have too high a solubility, and the copper is quickly leached out of the wood and contaminates the environment rather than protects the wood. Too low a solubility, and the copper salts (and copper oxides) are not bioactive. The dissolution rate/leach rate of the sparingly soluble copper salts used in the particulates will be a function of 1) the solubility of the sparingly soluble copper salt(s) in the leachant; 2) the surface area of the sparingly soluble copper salts available to contact the leachant, 3) the energy of the crystal which must be overcome to dissolve ions from the crystal lattice, and 4) the flow characteristics of the leachant in the wood matrix, especially regarding boundary layer effects. Each of these properties plays a role in every flowrate scenario, but some are more dominant than others at certain times. We believe the leach rates will be primarily governed by the solubility of the sparingly soluble salts and by boundary layer effects of the copper and counterions diffusing from the particulates in regimes where the leachant is moving extremely slowly, e.g., less than a few millimeters per day. At intermediate leachant flow rates, we believe the leach rate of copper will depend on primarily on the available surface area. At higher rates, such as found in the standard test methods typically used by industry, the leach rates will be governed more by the available surface area of the sparingly soluble salts and by the energy of the crystal lattice.

Dissolution is a function not only of the pH of the water within the wood and the solubility product value for the particular salts, but also on dynamic conditions. Since the copper is present in the wood as particulates, dissolution of copper will also be restricted by the low surface area of the particles. Larger particulates will reduce the leaching rate in most leachant flow regimes. The dissolution of larger particulates is more dependent on surface effects than is the dissolution of smaller particulates, in part because the available surface area is lower for larger particulates. At low flow rates, boundary layer effects may multiply the effects of lower surface area, but at typical leach test flow regimes boundary layer effects may be minimized if the flow of the leachant through the wood matrix is turbulent.

At low flow rates, the p of the leachant will be modified by the dissolution of the copper hydroxides and the copper carbonates. The isoelectric point of copper hydroxide is about 11, making copper hydroxide a very effective base. The presence of other basic salts, for example phosphate ions, can further hinder leach rates. At high leachant flow rates, however, such as are used in standard leachant tests, the flow rates are such that the presence of hydroxides, phosphates, and the like are minimized.

Since the leachant flow rates of wood in use can be highly variable, the copper-based particulates advantageously provide a wide range of coverage over many environments by having 1) a wide distribution of particle sizes, 2) having sparingly soluble salts of differing solubilities, or 3) both.

The biocidal compositions of this invention can be used in foliar applications, in a variety of industrial applications, and in wood applications. Generally, the biggest differences between foliar applications and wood treatment are the particle size distribution must be narrower for injecting into wood than for spreading on fields. A composition having a d50 of 0.35 microns can be used in either a foliar application or a wood application. The advantages of excellent coverage and reduced treatment concentrations can be achieved if the $d_{90}$ is within about 3 times the $d_{50}$, and the $d_{99}$ can be any number. Unmilled copper salts having a $d_{50}$ of 0.2 microns were useful for foliar applications, and indeed that is the commercial purpose of that formulation. For wood injection, on the other hand, the $d_{96}$ should be less that 3 times the $d_{50}$, preferably the $d_{98}$ is less that 3 times the $d_{50}$, more preferably the $d_{99}$ is less that 3 times the $d_{50}$. Additionally, different inorganic biocidal salts and different organic biocides may be selected for embodiments where the particles are exposed to sun and rain, versus those selected for the more protected environment within wood.

Another aspect of the invention relates a method of preserving wood or a wood product comprising injecting into wood or dispersing into a wood product one or more of the biocidal particulates of this invention. The material of this invention is useful for wood, and also for wood products, e.g., wood composites. Exemplary wood products include oriented strand board, particle board, medium density fiberboard, plywood, laminated veneer lumber, laminated strand lumber, hardboard and the like. Preferred methods of preserving wood composites require the preservative of this invention either be mixed with the wood material or fibers before bonding, or more preferably injected into the wood material or fibers, followed by bonding.

In one embodiment, the wood or wood product has a surface, a thickness, a width, and a length. Preferably, the wood or wood product comprises a homogenous distribution of copper-based particles of the invention. In one embodiment, a volume number density of the copper-based particles 5 cm from the surface, and preferably throughout the interior of the wood or wood product, is at least about 50%, for example, at least about, 60%, 70%, or 75% a volume number density of the copper-based particles 1 cm from the surface.

Wood or wood products comprising copper-based particles in accordance with the present invention may be prepared by subjecting the wood to vacuum and/or pressure in the presence of a flowable material comprising the copper-based particles. A pre-injection of carbon dioxide followed by vacuum and then injection of the slurry is a preferred method of injecting the slurry into wood. Injection of particles into the wood or wood product from a flowable material comprising the particles may require longer pressure treatments than would be required for liquids free of such particles. Pressures of, for example, at least about 75 psi, 100 psi, or 150 psi may be used. Exemplary flowable materials include liquids comprising copper-based particles, emulsions comprising copper-based particles, and slurries comprising copper-based particles.

EXAMPLES

The following examples are merely indicative of the nature of the present invention, and should not be construed as limiting the scope of the invention, nor of the appended claims, in any manner.

Example 1

Milling Chlorothalonil with 0.5 mm Zirconium Silicate

The laboratory-sized vertical mill was provided by CB Mills, model# L-3-J. The mill has a 2 liter capacity and is jacketed for cooling. Unless otherwise specified, ambient water was cycled through the mill cooling jacket during operation. The internal dimensions are 3.9" diameter by 9.1" height. The mill uses a standard 3×3" disk agitator (mild steel) on a stainless steel shaft, and it operates at 2,620 rpm.

The media used in this Example was 0.4-0.5 mm zirconium silicate beads supplied by CB Mills. All particle size determinations were made with a Sedigraph™ 5100T manufactured by Micromeritics, which uses x-ray detection and bases calculations of size on Stokes' Law.

The formulation contained 20.41% chlorothalonil (98% active), 5% Galoryl™ DT-120, 2% Morwet™ EFW, and 72.6% water by weight, and the concentrate had a pH of 8.0. The total batch weight was about 600 g. The results of a 7.5 hour grinding study are given in Table 1 below.

TABLE 1

| Milling Time | $d_{50}$ | Particle Size Data-Volume % With Diamter Greater Than | | | |
|---|---|---|---|---|---|
| Mins. | μm | 10 μm | 5 μm | 2 μm | 1 μm |
| 0 | 4.9 | 10 | 48 | 95 | |
| 30 | 1.3 | 0 | 4 | 21 | 68 |
| 60 | 1.0 | 4 | 2 | 11 | 50 |
| 90 | 1.4 | 18 | 23 | 22 | 94 |
| 120 | 1.03 | 2 | 0 | 4 | |
| 150 | 1.12 | 0 | 2 | 6 | 58 |
| 180 | 1.07 | 2 | 2 | 7 | 53 |
| 270 | 1.09 | 2 | 0 | 8 | 54 |
| 450 | 1.15 | 12 | 8 | 21 | 56 |

The results show that chlorothalonil can be wet milled from a starting particle size of about 3-4 microns to a $d_{50}$ near 1 micron within about one hour, using a spherical ~3.8 g/cm$^3$ zirconium silicate media having an average particle size of about 0.4-0.5 mm. Further grinding had little effect, possibly slightly reducing the weight of particles over about 2 microns and thereby reducing the $d_{90}$ from about 2 microns at 60 minutes to slightly less than 2.

However, these results also showed the limitations of this lower density material. In the next example, higher density doped zirconia, having a density of 5.5 to 6.5 g/cc, was used and provided much more effective milling.

Example 2

Milling Chlorothalonil with 0.5 mm Zirconium Oxide

The same mill and conditions were used in this experiment as in experiment 1. However, the grinding media was 0.5-0.6 mm cerium-doped zirconium oxide beads obtained from CB Mills. The density of the cerium doped zirconium oxide is ~6.0 g/cm$^3$. The formulation contained 20.41% chlorothalonil (98% Active), 5% Galoryl™ DT-120, 2% Morwet™ EFW, 3% Pluronic™ F-108, and 69.6% water by weight, and the concentrate had a pH of about 7.3. The total batch weight was about 600 g. The results are shown in Table 2 below.

TABLE 2

| Milling Time | $d_{50}$ | Particle Size Data-Volume % With Diamter Greater Than | | | | | |
|---|---|---|---|---|---|---|---|
| Mins. | μm | 10 μm | 5 μm | 2 μm | 1 μm | 0.4 μm | 0.2 μm |
| 0 | 3.44 | 8 | 30 | 77 | 92 | — | — |
| 90 | 0.31 | 3 | 3 | 3 | 3 | 22 | — |
| 240 | 0.21 | 0 | 1 | 2 | 3 | 3 | 51 |

For the higher density 0.5 mm zirconia milling media, a composition with a $d_{50}$ less than 1 micron and a $d_{95}$ less than 1 micron was obtainable in 90 minutes, and a composition with a $d_{50}$ less than 0.3 microns and a $d_{95}$ less than 0.4 microns was obtainable in 6 hours. The product obtained after 90 minutes of milling represents an increase in number of particles per unit of mass by a factor of more than about 30 over the standard products, but the product obtained after 90 minutes of milling represents an increase in number of particles per unit of mass by a factor of more than about 1000 over the standard products. The higher surface areas associated with the smaller particles should give rise to a product with enhanced bioactivity due to an increase in reservoir activity (ability to deliver chlorothalonil to the infection court).

Example 3

Milling Sparingly Soluble Copper Salts with 0.5 mm Zirconium Silicate

This comparative example and subsequent example show the effectiveness of the milling media and process on the particle size distribution of inorganic copper salts.

Comparative Example 3A

Figure 3:
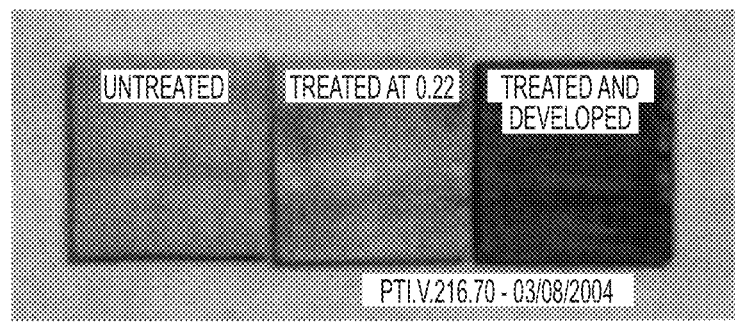

A commercially available a magnesium stabilized form of copper hydroxide particulate material, Champ DP® available from available from Phibro-Tech., Inc., has particles with a $d_{50}$ of about 0.2 microns. FIG. 3 shows the results of trying to inject untreated 2.5 micron $d_{50}$ copper hydroxide into wood. The copper material plugged the surface of the wood and made an unsightly blue-green stain. The results were less dramatic when injecting Champ DP, but were still commercially unacceptable. Analysis of the material found that while the d50 of the material was <0.2 microns, about 13% by weight of the material had diameters between 2 and 5 times greater than the $d_{50}$, and 1% had an even greater diameter.

The Champ DP® material was placed in a mill with about a 50% by volume loading of 2 mm zirconium silicate milling beads. Samples were removed intermittently and the particle size distribution was determined. Wet milling with 2 mm zirconium silicate milling media had no effect—wet milling for days resulted in only a very slight decrease in particle size, a small shift in the particle size distribution, but the material was not injectable into wood In contrast, five samples of particulate copper salts made following standard procedures known in the art were milled according to the method of this invention. The first two samples were copper hydroxide—one with an initial particle size $d_{50}$ of <0.2 microns (the material of comparative example A), and the second with an initial $d_{50}$ of 2.5 microns. A basic copper carbonate (BCC) salt was prepared and it had an initial $d_{50}$ of 3.4 microns. A tribasic copper sulfate salt was prepared and this material has a $d_{50}$ of 6.2 micron. Finally, a copper oxychloride (COc) sample was prepared and this material has an initial $d_{50}$ of 3.3 microns. Selected surface active agents were added to each slurry, and the initial slurries were each in turn loaded into a ball mill having 0.5 mm zirconium silicate (density 3.8 grams/cm3) at about 50% of mill volume, and milled at about 2600 rpm for about a half an hour. The particle size distribution of the milled material was then determined. The particle size distribution data is shown in Table 1. It can be seen that even with the relatively modest zirconium silicate milling media, injectable compositions were obtained in about 30 minutes milling time or less.

TABLE 1

Particle Size Distribution Before/After Millnig (0.5 mm Zirconium Silicate)

| Material | d50 | % <10μ | % <1μ | % <0.4μ | % <0.2μ |
|---|---|---|---|---|---|
| $Cu(OH)_2$, before milling | <0.2 | 99% | 84% | 64% | 57% |
| $Cu(OH)_2$, after milling | <0.2 | 99% | 97% | 95% | 85% |
| Cu(OH)2, before milling | 2.5 | 99% | 9% | — | — |
| Cu(OH)2, after milling | 0.3 | 99.7% | 95% | 22% | —% |
| BCC*, before milling | 3.4 | 98% | 1.2% | — | — |
| BCC*, after milling | <0.2 | 99% | 97% | 97% | 87% |
| TBS*, before milling | 6.2 | 70% | 17% | — | — |
| TBS*, after milling | <0.2 | 99.5% | 96% | 91% | 55% |
| COc*, before milling | 3.3 | 98.5% | 3% | — | — |
| COc*, after milling | 0.38 | 99.4% | 94% | 63% | — |

It can be seen that even the less effective milling media, ~0.5 mm zirconium silicate, was useful for milling sparingly soluble copper salts to the sub-micron particle size distribution needed for treating wood, for incorporating into non-fouling paints and coatings, and for foliar treatments. Further, the rate of particle size attrition is so great that there is no need to use expensive precipitation techniques to provide a feedstock having a sub-micron $d_{50}$. The initial d50 ranged from 0.2 microns to over 6 microns, but after 30 minutes or less of milling each of the above milled copper salts (milling about 15 to about 30 minutes) were injected into wood samples with no discernible plugging.

Milling with the more preferred zirconium oxide milling beads will provide a smaller d50 and will further reduce the amount of material, if any, having a diameter greater than 1 micron. Particulate biocides have an advantage over dispersed or soluble biocides in that the material leaches more slowly from wood than would comparable amounts of soluble biocides, and also about the same or more slowly than comparable amounts of the same biocide applied to the same wood as an emulsion.

Example 4

Injecting Milled Copper Salt Slurries into Wood

Slurries of the above milled sparingly soluble copper salts were successfully injected into standard 1" cubes of Southern Yellow Pine wood. The injection procedures emulated standard conditions used in the industry.

FIG. 3 shows representative photographs showing the comparison of the unacceptable product, which had a $d_{50}$ of 2.5 microns yet still plugged the wood, is shown in comparison with blocks injected with the product milled according to the process of this invention as described in Example 3. FIG. 3 shows the clean appearance of the wood blocks injected with the milled copper hydroxide, to compare with the photograph of the wood samples injected with the un-milled ($d_{50}$<0.2 micron) copper hydroxide. Unlike the blocks injected with un-milled material, wood blocks injected with milled material showed little or no color or evidence of injection of copper-containing particulate salts.

Copper development by colorimetric agents (dithio-oxamide/ammonia) showed the copper to be fully penetrated across the block in the sapwood portion. FIG. 1 shows the penetration of injected particulate copper hydroxide developed with dithio-oxamide in the third picture. The stain corresponds to copper. It can be seen in FIG. 1 that the copper is evenly dispersed throughout the wood. Subsequent acid leaching and quantitative analysis of the copper from two blocks showed that loadings of about 95% and about 104% of expectation (or essentially 100% average of expectation) had occurred. At 100% loading, values of 0.22 lb/ft$^3$ of copper would be obtained.

Example 5

Leaching Copper from Treate Wood

Copper leaching rates from the wood samples prepared in Example 4 were measured following the AWPA Standard Method E11-97. There are two comparative examples— leaching data was obtained from a wood block preserved with a prior art soluble solution of copper MEA carbonate and from a prior art wood block preserved with CCA. The leach rates of the various wood blocks treated with the preservatives prepared according to this invention were far below the leach rates of wood treated with soluble copper carbonate and were even below leach rates of samples treated with CCA.

Figure 2:
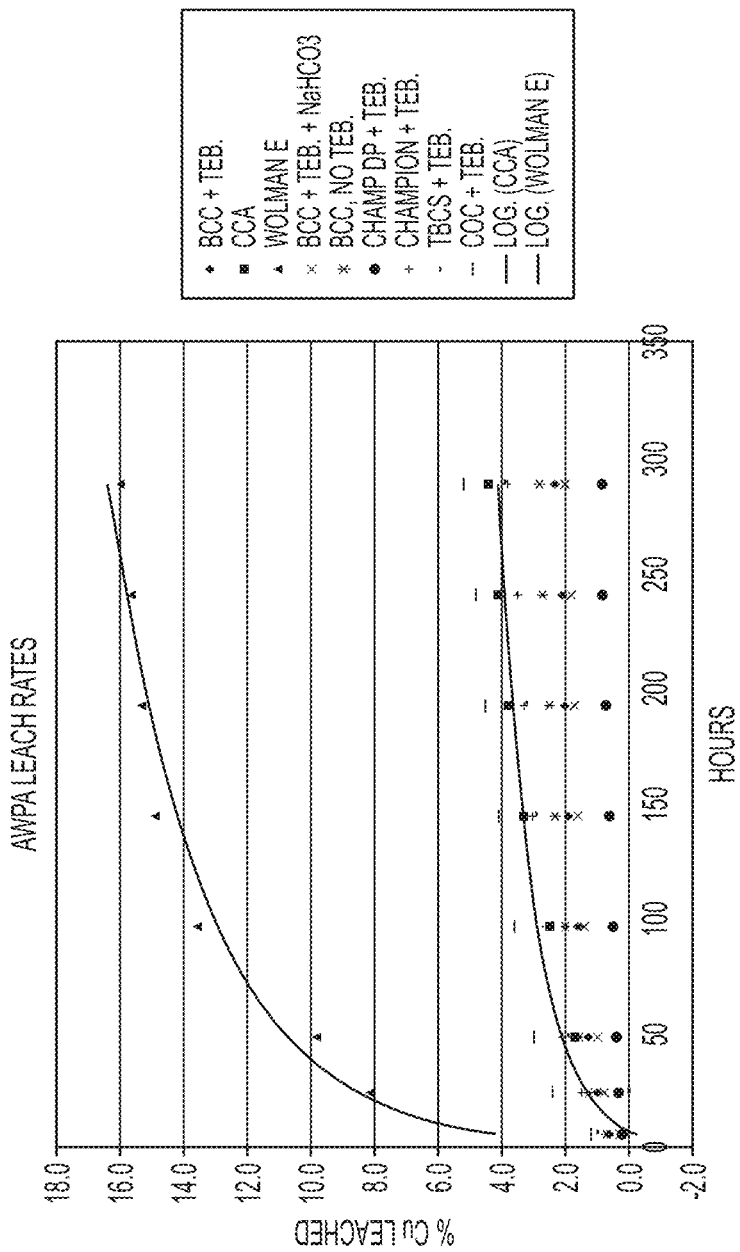

Leaching data from wood was measured following the AWPA Standard Method E11-97 for the following preservative treatments, where, unless specified, the tebuconazole (TEB) concentration was added as an emulsion at 3% of the weight of the added copper: A) TEB and injected basic copper carbonate particulates; B) traditionally CCA-treated wood (as a control); C) TEB and copper methanolamine carbonate (as a control, believed to approximate the currently available Wolman E treatment); D) TEB and injected basic copper carbonate particulates and with sodium bicarbonate buffer; E) Injected basic copper carbonate particulates; F) TEB and injected copper hydroxide particulates modified with zinc and magnesium; G) about 5% TEB and injected copper hydroxide particulates modified with phosphate coating; H) TEB and injected tribasic copper sulfate particulates; and I) TEB and injected copper oxychloride particulates. The leaching data for the various particulate slurries and from two controls are shown in FIG. 2.

The total copper leached from wood preserved with copper-MEA-carbonate was 5.7% at 6 hours, 8.5% at 24 hours, 11% at 48 hours, 22% at 96 hours, 36% at 144 hours, 49% at 192 hours, 62% at 240 hours, 69% at 288 hours, and 76% at 336 hours. The amount of copper leached from copper hydroxide particulates was 0.4% at 6 hours, 0.6% at 24 hours, 0.62% at 48 hours, 1.0% at 96 hours, 1.6% at 144 hours, 2.1% at 192 hours, 3.2% at 240 hours, 3.4% at 288 hours, and 3.7% at 336 hours. The difference in leach rate was greater than a factor of 20.

The leaching data is generally consistent within the small amount of copper leached from these wood samples. Using the copper leach rate of CCA as a standard, and viewing the total leached copper at 96 and 240 hours as representative, the leach rate ratios given by the "total leached copper to total CCA-leached copper" is given in Table 3 below.

Of the sparingly soluble salts used, the leach rate, in descending order, is as follows: copper MEA carbonate (comparative)>>copper oxychloride>tribasic copper sulfate and/or copper hydroxide with phosphate>basic copper carbonate>copper hydroxide with Zn and Mg. The isoelectric point of copper oxychloride is about 5 to about 5.5, and the isoelectric point of tribasic copper sulfate is about 6 to about 6.5. As these materials are very poor bases, the higher leach rates from the materials is consistent with expected higher solubility at lower pH values. The presence of TEB reduced leach rates from basic copper carbonate by about 20%, most likely due to TEB partially coating particulates. A buffering system, sodium bicarbonate, reduced the leach rates from TEB/basic copper carbonate by about 10% relative to a preservative without the buffer.

Use of the small diameter milling material, preferably 0.3 mm to 0.6 mm, is essential to make a product that can be confidently sold for injection into wood.

Example 5

Toxicity Test

A sample of treated wood was sent to an outside source for short-duration toxicity testing. The results suggest there is no difference in the Threshold Toxicity between wood treated with a copper MEA carbonate/tebuconazole formulation and wood treated with a identical loading of basic copper carbonate particles of this invention admixed (and partially coated with) the same quantity of tebuconazole.

The invention is meant to be illustrated by these examples, but not limited to these examples.

TABLE 3

| Ex. | Description of Preservative System | 96 hr. ratio to CCA | 240 hr. ratio to CCA |
|---|---|---|---|
| A | 3% TEB and basic copper carbonate particulates | 0.67:1 | 051:1 |
| C | 3% TEB and copper MEA carbonate (comparative) | 5.2:1 | 3.85:1 |
| D | 3% TEB and basic copper carbonate particulates with sodium bicarbonate buffer | 0.54:1 | 0.46:1 |
| E | basic copper carbonate particulates | 0.77:1 | 0.63:1 |
| F | 3% TEB and copper hydroxide with Zn and Mg particulates | 0.2:1 | 0.19:1 |
| G | 5% TEB and copper hydroxide particulates modified with phosphate coating | 1.0:1 | 0.88:1 |
| H | 3% TEB and tribasic copper sulfate particulates | 0.96:1 | 0.88:1 |
| I | 3% TEB and copper oxychloride particulates | 1.4:1 | 1.17:1 |

What is claimed is:

1. An aqueous wood preservative slurry, herein said slurry comprises a plurality of injectable first particulates of a solid copper compound, wherein the first particulates have a $d_{96}$ of about 1 micron or less, a $d_{99}$ of about 1.5 microns or less, and a $d_{50}$ of greater than 0.02 microns.

2. The aqueous wood preservative slurry of claim 1, wherein the $d_{50}$ is between about 0.05 microns and about 0.5 microns.

3. The aqueous wood preservative slurry of claim 1, wherein the $d_{50}$ is between about 0.1 microns and about 0.3 microns.

4. The aqueous wood preservative slurry of claim 1, wherein the copper compound is selected from the group consisting of copper borate, basic copper carbonate, copper hydroxide, and a combination thereof.

5. The aqueous wood preservative slurry of claim 1, wherein the copper compound is selected from the group consisting of tribasic copper sulfate, copper oxychloride, basic copper nitrate, basic copper phosphate, basic copper phosphosulfate, copper ferricyanide, copper ferricyanate, copper carbonate, copper borate, copper silicate, copper fluorosilicate, copper thiocyanate, copper boride and a combination thereof.

6. The aqueous wood preservative slurry of claim 1, wherein the $d_{96}$ of the first particulates is about 0.5 micron or less, the $d_{99}$ is about 1 microns or less, and the $d_{50}$ is between 0.05 microns and 0.4 microns.

7. The aqueous wood preservative slurry of claim 1, wherein said injectable first particulates are wet-milled in the presence of a liquid comprising a surface active agent and an effective amount of milling beads having a diameter between 0.1 mm and 0.8 mm and a density greater than about 3 grams/$cm^3$.

8. The aqueous wood preservative slurry of claim 1, wherein said aqueous wood preservative slurry further comprises an organic biocide, wherein at least a portion of the organic biocide is coated on the first particulates.

9. The aqueous wood preservative slurry of claim 1, wherein said aqueous wood preservative slurry further comprises a plurality of injectable second particulates comprising a sparingly soluble in water organic biocide, wherein the second particulates have a $d_{96}$ of about 1 micron or less and a $d_{99}$ of about 1.5 microns or less.

10. The aqueous wood preservative slurry of claim 9, wherein the $d_{96}$ of the second particulates is about 0.5 micron or less, the $d_{50}$ is between about 0.05 microns and about 0.4 microns.

11. The aqueous wood preservative slurry of claim 9, wherein the organic biocide is selected from the group consisting of amitraz, deltamethrin, bifenthrin, chlorpyrifos, chlorpyrifosmethyl, cyfluthrin, cypermethrin, tralomethrin, betacyfluthrin, cyhalothrin, lambda-cyhalothrin, alpha-cypermethrin, triazophos, beta-cypermethrin, cyphenothrin, permethrin, phenothrin, cyproconazole, tetraconazole, dodemorph, difenoconazole, dimethomorph, fenarimol, diniconazole, myclobutanil, etridiazole, penconazole, flusilazole, prochloraz, imibenconazole, triadimefon, propiconazole, azaconazole, tebuconazole, epoxyconazole, tridemorph, penpropimorph, trifluinizole, chlorothalonil, imidacloprid, 3-iodo-2-propynyl butylcarbamate, fludioxonil, azoxystrobin, thiabendazole, cyprodinil, isothiazolone, quaternary ammonium compound, and a combination thereof.

12. The aqueous wood preservative slurry of claim 11, wherein the quaternary ammonium compound is selected from the group consisting of didecyldimethylammonium salt, benzyldimethyltetradecylammonium chloride, benzyldimethyldodecylammonium chloride, and didecyldimethylammonium chloride.

13. The aqueous wood preservative slurry of claim 1, wherein the aqueous wood preservative slurry further comprises a plurality of injectable third particulates of a solid zinc compound, solid zinc oxide, solid iron oxide, or any mixture thereof, wherein the third particulates have a $d_{96}$ of about 1 micron or less and a $d_{99}$ of about 1.5 microns or less.

14. The aqueous wood preservative slurry of claim 13, wherein the zinc compound is selected from the group consisting of zinc hydroxide; basic zinc carbonate, basic zinc phosphate, zinc borate, zinc oxychloride, zinc fluoroborate, zinc carbonate, zinc orthophosphate, zinc fluoride, and a combination thereof.

15. The aqueous wood preservative slurry of claim 1, wherein said copper compound is a copper oxide.

* * * * *